US010653295B2

(12) United States Patent
Ebata

(10) Patent No.: US 10,653,295 B2
(45) Date of Patent: May 19, 2020

(54) IMAGE PROCESSING APPARATUS, ENDOSCOPE SYSTEM, AND IMAGE PROCESSING METHOD

(71) Applicant: FUJIFILM Corporation, Tokyo (JP)

(72) Inventor: Tetsuro Ebata, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 149 days.

(21) Appl. No.: 15/937,871

(22) Filed: Mar. 28, 2018

(65) Prior Publication Data
US 2018/0214005 A1 Aug. 2, 2018

Related U.S. Application Data

(63) Continuation of application No. PCT/JP2016/078818, filed on Sep. 29, 2016.

(30) Foreign Application Priority Data

Sep. 29, 2015 (JP) ................................. 2015-192005

(51) Int. Cl.
*A61B 1/00* (2006.01)
*A61B 5/1455* (2006.01)
(Continued)

(52) U.S. Cl.
CPC ........ *A61B 1/00009* (2013.01); *A61B 1/0005* (2013.01); *A61B 1/04* (2013.01);
(Continued)

(58) Field of Classification Search
CPC . A61B 5/02007; A61B 5/0205; A61B 5/0261; A61B 5/1032; A61B 5/107;
(Continued)

(56) References Cited

U.S. PATENT DOCUMENTS

2009/0203977 A1 8/2009 Backman et al.
2011/0245642 A1 10/2011 Minetoma
(Continued)

FOREIGN PATENT DOCUMENTS

EP 2896363 7/2015
JP H10-14864 1/1998
(Continued)

OTHER PUBLICATIONS

"Search Report of Europe Counterpart Application", dated Sep. 6, 2018, p. 1-p. 8.
(Continued)

*Primary Examiner* — Leon Flores
(74) *Attorney, Agent, or Firm* — JCIPRNET

(57) ABSTRACT

An image processing apparatus includes: an image acquisition unit that acquires a plurality of endoscope images obtained by imaging an observation target at different times with an endoscope; a blood vessel extraction unit that extracts blood vessels from the plurality of endoscope images; a blood vessel index value calculation unit that calculates a blood vessel index value for each of the blood vessels extracted from the endoscope images; a temporal change calculation unit that calculates a temporal change of the blood vessel index value; a determination unit that determines a state of a mucous membrane of the observation target using the temporal change of the blood vessel index value; and a monitor that displays a determination result of the determination unit.

17 Claims, 15 Drawing Sheets

(51) Int. Cl.
| | |
|---|---|
| *A61B 5/107* | (2006.01) |
| *A61B 1/04* | (2006.01) |
| *A61B 5/02* | (2006.01) |
| *A61B 5/0205* | (2006.01) |
| *A61B 5/026* | (2006.01) |
| *A61B 5/103* | (2006.01) |
| *A61B 5/1459* | (2006.01) |
| *A61B 5/00* | (2006.01) |

(52) U.S. Cl.
CPC ........ *A61B 5/0205* (2013.01); *A61B 5/02007* (2013.01); *A61B 5/0261* (2013.01); *A61B 5/107* (2013.01); *A61B 5/1032* (2013.01); *A61B 5/1079* (2013.01); *A61B 5/1455* (2013.01); *A61B 5/1459* (2013.01); *A61B 5/489* (2013.01); *A61B 5/4842* (2013.01); *A61B 5/7278* (2013.01)

(58) Field of Classification Search
CPC ... A61B 5/1079; A61B 5/1455; A61B 5/1459; A61B 5/4842; A61B 5/489; A61B 5/7278; A61B 1/000096; A61B 1/0005; A61B 1/04
See application file for complete search history.

(56) References Cited

U.S. PATENT DOCUMENTS

| | | |
|---|---|---|
| 2012/0289801 A1 | 11/2012 | Yamaguchi |
| 2014/0148658 A1 | 5/2014 | Zalevsky et al. |
| 2015/0181185 A1 | 6/2015 | Ikemoto et al. |
| 2015/0356369 A1* | 12/2015 | Kitamura ................ G06K 9/46 382/128 |
| 2016/0157763 A1 | 6/2016 | Tominaga |

FOREIGN PATENT DOCUMENTS

| | | |
|---|---|---|
| JP | 2002-165757 | 6/2002 |
| JP | 2006-218138 | 8/2006 |
| JP | 2007-061638 | 3/2007 |
| JP | 2009-207541 | 9/2009 |
| JP | 2011-217798 | 11/2011 |
| JP | 2011-255006 | 12/2011 |
| JP | 2012-514525 | 6/2012 |
| JP | 2012-235926 | 12/2012 |
| JP | 2014-018333 | 2/2014 |
| JP | 2015-066129 | 4/2015 |
| WO | 2014132694 | 9/2014 |

OTHER PUBLICATIONS

"International Search Report (Form PCT/ISA/210) of PCT/JP2016/078818", dated Dec. 20, 2016, with English translation thereof, pp. 1-4.

"International Preliminary Examination Report(Form PCT/IPEA/409)", dated Oct. 23, 2017, with English translation thereof, pp. 1-20.

"Office Action of Japan Counterpart Application," dated Jun. 11, 2019, with English translation thereof, p. 1-p. 8.

"Notification of Reasons for Refusal of Japan Counterpart Application," dated Oct. 25, 2018, with English translation thereof, p. 1-p. 6.

* cited by examiner

IMAGE PROCESSING APPARATUS, ENDOSCOPE SYSTEM, AND IMAGE PROCESSING METHOD

CROSS-REFERENCE TO RELATED APPLICATIONS

This application is a Continuation of PCT International Application No. PCT/JP2016/078818 filed on Sep. 29, 2016, which claims priority under 35 U.S.C § 119(a) to Japanese Patent Application No. 2015-192005 filed on Sep. 29, 2015. The above application is hereby expressly incorporated by reference, in its entirety, into the present application.

BACKGROUND OF THE INVENTION

1. Field of the Invention

The present invention relates to an image processing apparatus, an endoscope system, and an image processing method for assisting diagnosis by calculating data, which is to be used for diagnosis, using an endoscope image captured by an endoscope.

2. Description of the Related Art

In the medical field, diagnosis using an endoscope system including a light source device, an endoscope, and a processor device has been widely performed. In the diagnosis using the endoscope system, an insertion part of the endoscope is inserted into a subject, illumination light is emitted from the distal end portion, and an observation target irradiated with the illumination light (mucous membrane or the like inside the subject) is imaged by an imaging sensor mounted in the distal end portion of the endoscope. Then, an image (hereinafter, referred to as an endoscope image) of the observation target is generated using an image signal obtained by the imaging, and is displayed on the monitor.

Usually, in the endoscope system, an endoscope image in which the observation target can be observed with a natural color shade (hereinafter, referred to as a normal light image) is displayed by imaging the observation target irradiated with white illumination light (also referred to as normal light). In addition, an endoscope system that obtains an endoscope image (hereinafter, referred to as a special observation image) emphasizing a blood vessel, a pit pattern, and the like of the observation target by using light having a specific wavelength range as illumination light has also become widespread. In the case of performing diagnosis using an endoscope image, information of blood vessels, pit patterns, and the like is an important diagnostic material. Therefore, special observation images emphasizing these are particularly useful for diagnosis.

In recent years, an endoscope system or a diagnostic assistance apparatus is known that assists a doctor's diagnosis not only by emphasizing the blood vessel but also by calculating the depth, thickness, density, and the like of blood vessels using an endoscope image (or an image signal used to generate an endoscope image) (JP2007-061638A and JP2011-217798A (corresponding to US2011/245642A1)). There is also known a system that assists diagnosis by displaying a temporal change of information regarding a blood vessel (hereinafter, referred to as blood vessel information) that can be calculated using an endoscope image, such as the density of blood vessels (JP2012-235926A (corresponding to US2012/289801A1) and JP2015-066129A (corresponding to US2016/157763A1)).

For example, in the system disclosed in JP2012-235926A, a temporal change in oxygen saturation that is one of blood vessel information is displayed on a monitor in real time. In the system disclosed in JP2015-066129A, a temporal change in the intensity of the fluorescence emitted from the observation target is graphically emitted.

There is also known an endoscope system or the like that assists diagnosis by calculating the feature amount of an endoscope image and determining or classifying a lesion using the calculated feature amount (JP2002-165757A and JP1998-014864A (JP-H10-014864A)). There is also known an endoscope system or the like that emphasizes a lesion is by changing the color of a pixel determined to be a lesion or superimposing an alert image on the lesion (JP2014-018333A (corresponding to US2015/181185A1) and JP2011-255006A).

SUMMARY OF THE INVENTION

Since blood vessel information, such as the density of blood vessels or oxygen saturation, is highly important information that can be a deciding factor in diagnosis using an endoscope image, it is possible to assist diagnosis by calculating blood vessel information as in the endoscope systems disclosed in JP2007-061638A, JP2011-217798A, JP2012-235926A, and JP2015-066129A. In particular, in JP2012-235926A and JP2015-066129A, a temporal change of blood vessel information is displayed. Accordingly, since it is possible to assist diagnosis even in a case where definitive determination cannot be made unless the temporal change of blood vessel information as well as the value of blood vessel information is known, the effect of diagnostic assistance effect is particularly high.

However, how to grasp the blood vessel information calculated by the endoscope system or the like and determine or classify the lesion is left to the knowledge or experience of the doctor. Therefore, the burden at the time of diagnosis is still large. For this reason, the endoscope system or the like for calculating blood vessel information is required to assist diagnosis more effectively by using information that is more directly related to diagnosis.

On the other hand, in JP2002-165757A and JP1998-014864A (JP-H10-014864A), the feature amount of the endoscope image is calculated, the lesion is determined or classified using the calculated feature amount, and the result (assumed diagnosis name or the like) is displayed. Therefore, information that is directly related to diagnosis is presented. However, since the feature amounts calculated in JP2002-165757A and JP1998-014864A (JP-H10-014864A) are feature amounts relevant to the tone of the mucosal surface or the structural pattern (mainly, directivity) of the pattern, determination or classification of a lesion, for which blood vessel information serves as a guide for diagnosis, is difficult. In addition, the feature amount is calculated using one endoscope image, and the temporal change of the observation target (in particular, blood vessel information) is not taken into consideration at all for determination or classification of a lesion.

It is an object of the present invention to provide an image processing apparatus, an endoscope system, and an image processing method for assisting diagnosis more directly and effectively than in the related art by determining the state of the mucous membrane of an observation target in consideration of a temporal change of the blood vessel of the observation target and displaying the result.

An image processing apparatus of the present invention comprises: an image acquisition unit that acquires a plurality of endoscope images obtained by imaging an observation target at different times with an endoscope; a blood vessel extraction unit that extracts blood vessels of the observation target from the plurality of endoscope images; a blood vessel index value calculation unit that calculates a plurality of types of a blood vessel index value for each of the blood vessels extracted from the endoscope images; a temporal change calculation unit that calculates a temporal change of the blood vessel index value for each type of the blood vessel index value; a determination unit that determines a state of a mucous membrane of the observation target using the temporal change for each type of the blood vessel index value; and a display unit that displays a determination result of the determination unit.

The blood vessel index value calculation unit may calculate, as the blood vessel index value, any blood vessel information of the number of blood vessels extracted by the blood vessel extraction unit, a thickness, a change in thickness, complexity of thickness change, a length, a change in length, the number of branches, a branching angle, a distance between branch points, the number of crossings, an inclination, an area, a density, a depth with respect to a mucous membrane as a reference, a height difference, an interval, a contrast, a color, a color change, a degree of meandering, blood concentration, oxygen saturation, a proportion of arteries, a proportion of veins, concentration of administered coloring agent, a running pattern, and a blood flow rate.

It is preferable that the blood vessel index value calculation unit comprises: a blood vessel information calculation unit that calculates any blood vessel information of the number of blood vessels extracted by the blood vessel extraction unit, a thickness, a change in thickness, complexity of thickness change, a length, a change in length, the number of branches, a branching angle, a distance between branch points, the number of crossings, an inclination, an area, a density, a depth with respect to a mucous membrane as a reference, a height difference, an interval, a contrast, a color, a color change, a degree of meandering, blood concentration, oxygen saturation, a proportion of arteries, a proportion of veins, concentration of administered coloring agent, a running pattern, and a blood flow rate; and a blood vessel parameter calculation unit that calculates a blood vessel parameter by calculation using a plurality of pieces of the blood vessel information and that the blood vessel index value calculation unit sets the blood vessel parameter as the blood vessel index value.

It is preferable that the temporal change calculation unit calculates a difference, a ratio, or a change rate between a plurality of the blood vessel index values.

It is preferable that the determination unit determines the state of the mucous membrane of the observation target based on a combination of temporal changes of the blood vessel index values in a plurality of time sections.

It is preferable that the determination unit calculates a length of a period during which the blood vessel index value is equal to or greater than a threshold value or the blood vessel index value is less than the threshold value and determines the state of the mucous membrane of the observation target based on the calculated length of the period.

It is preferable that, in a case of setting a region of interest in the plurality of endoscope images, the blood vessel index value calculation unit not only calculates the blood vessel index value of the region of interest but also calculates the blood vessel index value of a region outside the region of interest, the temporal change calculation unit calculates a spatial change of the blood vessel index value using the blood vessel index values of the inside and outside of the region of interest, and calculates a temporal change of the spatial change of the blood vessel index value, and the determination unit determines the state of the mucous membrane based on the temporal change of the spatial change of the blood vessel index value.

It is preferable that the determination result of the determination unit is displayed in a pop-up manner on the display unit.

It is preferable that the display setting of the pop-up display is performed using the temporal change of the blood vessel index value.

It is preferable that the endoscope image in which a portion where the state of the mucous membrane has been determined using the determination result of the determination unit is colored is displayed on the display unit.

It is preferable that, on the display unit, a color of a portion to be colored in the endoscope image is set using the temporal change of the blood vessel index value.

It is preferable that a list of the determination result of the determination unit is displayed on the display unit.

It is preferable that display setting of the list is performed using the temporal change of the blood vessel index value.

It is preferable that a portion where the state of the mucous membrane of the endoscope image has been determined is displayed in an enlarged manner on the display unit.

It is preferable that an enlargement ratio of the portion where the state of the mucous membrane of the endoscope image has been determined is set using the temporal change of the blood vessel index value.

An endoscope system of the present invention comprises: an endoscope that images an observation target; a processor device having an image acquisition unit that acquires a plurality of endoscope images obtained by imaging the observation target at different times with the endoscope, a blood vessel extraction unit that extracts blood vessels of the observation target from the plurality of endoscope images, a blood vessel index value calculation unit that calculates a plurality of types of a blood vessel index value for each of the blood vessels extracted from the endoscope images, a temporal change calculation unit that calculates a temporal change of the blood vessel index value for each type of the blood vessel index value, and a determination unit that determines a state of a mucous membrane of the observation target using the temporal change for each type of the blood vessel index value; and a display unit that displays a determination result of the determination unit.

An image processing method of the present invention comprises: a step in which an image acquisition unit acquires a plurality of endoscope images obtained by imaging an observation target at different times with an endoscope; a step of extracting blood vessels of the observation target from the plurality of endoscope images; a step in which a blood vessel index value calculation unit calculates a plurality of types of a blood vessel index value for each of the blood vessels extracted from the endoscope images; a step in which a temporal change calculation unit calculates a temporal change of the blood vessel index value for each type of the blood vessel index value; and a step in which a determination unit determines a state of a mucous membrane of the observation target using the temporal change for each type of the blood vessel index value.

Since the image processing apparatus, the endoscope system, and the image processing method determines the state of the mucous membrane in consideration of the temporal change of the blood vessel of the observation target and displays the result, it is possible to assist diagnosis more directly and effectively than in the related art.

DESCRIPTION OF THE PREFERRED EMBODIMENTS

First Embodiment

Figure 1:
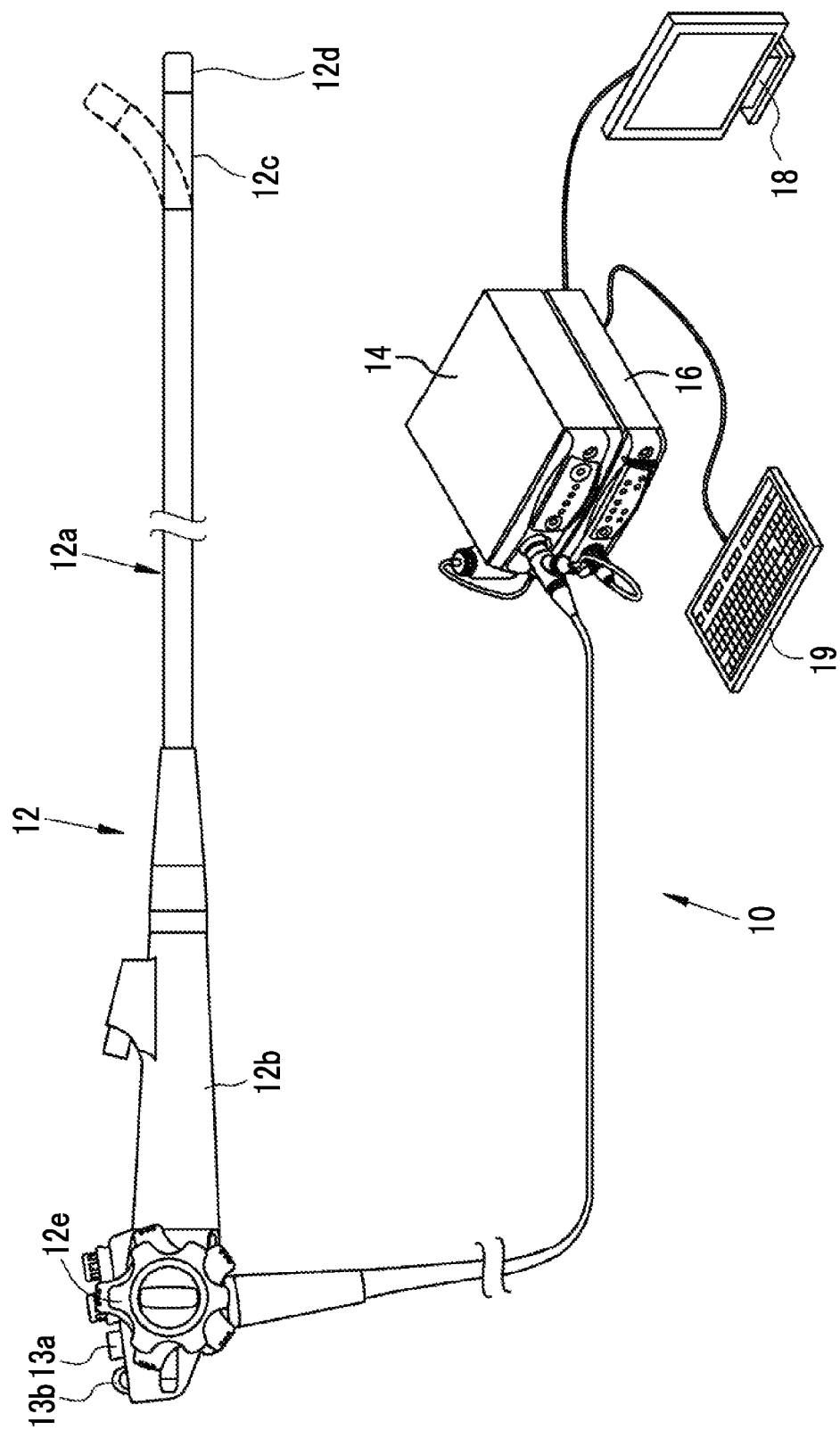
FIG. 1 is an external view of an endoscope system.

As shown in FIG. 1, an endoscope system 10 includes an endoscope 12, a light source device 14, a processor device 16, a monitor 18, and a console 19. The endoscope 12 is optically connected to the light source device 14, and is electrically connected to the processor device 16. The endoscope 12 includes an insertion part 12a that is inserted into a subject, an operation unit 12b provided in a proximal end portion of the insertion part 12a, and a bending portion 12c and a distal end portion 12d that are provided on the distal end side of the insertion part 12a. By operating an angle knob 12e of the operation unit 12b, the bending portion 12c is bent. Through the bending operation, the distal end portion 12d is directed in a desired direction.

In addition to the angle knob 12e, a still image acquisition instruction unit 13a and a zoom operation unit 13b are provided in the operation unit 12b. The still image acquisition instruction unit 13a operates in the case of inputting a still image acquisition instruction to the endoscope system 10. The instruction to acquire a still image includes a freeze instruction for displaying a still image of an observation target on the monitor 18 and a release instruction for storing a still image in a storage. The zoom operation unit 13b is used to input an imaging magnification change instruction for changing the imaging magnification.

The processor device 16 is electrically connected to the monitor 18 and the console 19. The monitor 18 outputs and displays an image of the observation target, information attached to the image, and the like. The console 19 functions as a user interface for receiving an input operation, such as a function setting.

Figure 2:
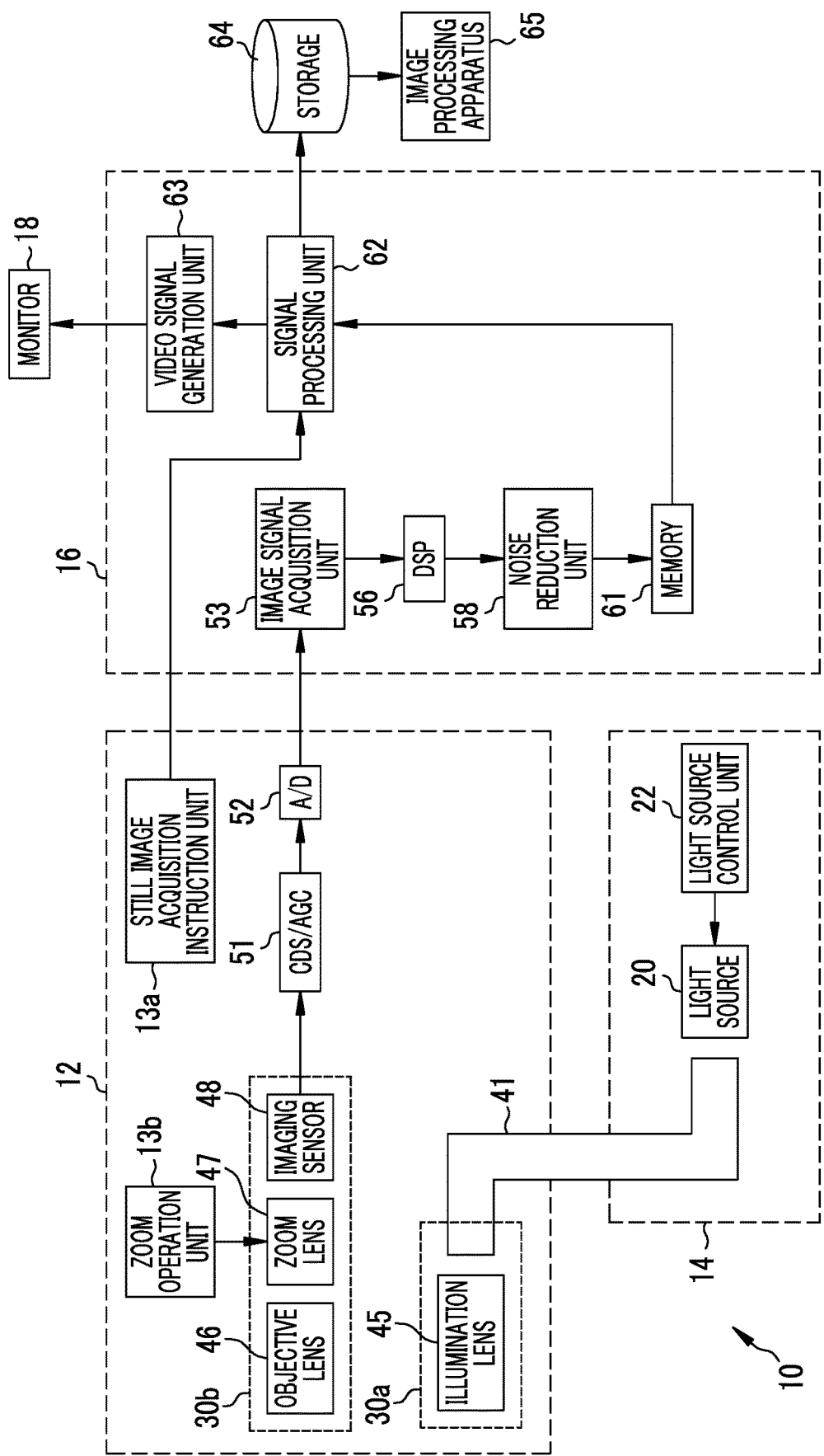
FIG. 2 is a block diagram of the endoscope system.

As shown in FIG. 2, the light source device 14 includes a light source 20 that emits illumination light to be emitted to the observation target and a light source control unit 22 that controls the light source 20. The light source 20 is, for example, a semiconductor light source such as a light emitting diode (LED) of a plurality of colors, a combination of a laser diode and a phosphor, or a halogen light source such as a xenon lamp. The light source 20 includes an optical filter for adjusting the wavelength range of light emitted from the LED or the like. The light source control unit 22 controls the amount of illumination light by ON/OFF of the LED or the like or by adjusting the driving current or the driving voltage of the LED or the like. In addition, the light source control unit 22 controls the wavelength range of illumination light by changing the optical filter or the like.

The endoscope system 10 has two types of observation modes, that is, a normal observation mode for observing an observation target in a normal observation image and a special observation mode for observing an observation target in a special observation image. In a case where the observation mode is a normal observation mode, the light source control unit 22 causes the light source 20 to generate approximately white illumination light. In a case where the observation mode is a special observation mode, the light source control unit 22 causes the light source 20 to generate illumination light having a specific narrow wavelength range (hereinafter, referred to as narrowband light). The observation mode is switched by a mode change switch (not shown) provided in the operation unit 12b.

The illumination light emitted from the light source 20 is incident on a light guide 41 inserted into the insertion part 12a. The light guide 41 is built into the endoscope 12 and a universal cord, and propagates the illumination light to the distal end portion 12d of the endoscope 12. The universal cord is a cord for connecting the endoscope 12 with the light source device 14 and the processor device 16. As the light guide 41, it is possible to use a multi-mode fiber. As an example, it is possible to use a small-diameter fiber cable having a diameter of ϕ0.3 mm to ϕ0.5 mm that includes a core with a diameter of 105 μm, a cladding with a diameter of 125 μm, and a protective layer as an outer skin.

An illumination optical system 30a and an imaging optical system 30b are provided in the distal end portion 12d of the endoscope 12. The illumination optical system 30a has an illumination lens 45, and the illumination light propagated by the light guide 41 is emitted to the observation target through the illumination lens 45. The imaging optical system 30*b* has an objective lens 46, a zoom lens 47, and an imaging sensor 48. Various kinds of light, such as reflected light, scattered light, and fluorescence from the observation target, are incident on the imaging sensor 48 through the objective lens 46 and the zoom lens 47. As a result, an image of the observation target is formed on the imaging sensor 48. The zoom lens 47 is moved freely between the telephoto end and the wide end by operating the zoom operation unit 13*b*, thereby enlarging or reducing the observation target formed on the imaging sensor 48.

The imaging sensor 48 is a color imaging sensor in which any one of red (R), green (G), and blue (B) color filters is provided for each pixel, and images the observation target and outputs the image signals of the respective colors of RGB. As the imaging sensor 48, it is possible to use a charge coupled device (CCD) imaging sensor or a complementary metal oxide semiconductor (CMOS) imaging sensor. Instead of the imaging sensor 48 in which primary color filters are provided, a complementary color imaging sensor including complementary color filters of cyan (C), magenta (M), yellow (Y), and green (G) may be used. In a case where a complementary color imaging sensor is used, image signals of four colors of CMYG are output. Therefore, by converting the image signals of four colors of CMYG into image signals of three colors of RGB by complementary color-primary color conversion, it is possible to obtain the same RGB image signals as in the imaging sensor 48. Instead of the imaging sensor 48, a monochrome sensor in which no color filter is provided may be used.

The image signal output from the imaging sensor 48 is transmitted to a CDS/AGC circuit 51. The CDS/AGC circuit 51 performs correlated double sampling (CDS) or automatic gain control (AGC) for the image signal that is an analog signal. The image signal transmitted through the CDS/AGC circuit 51 is converted into a digital image signal by an analog to digital (A/D) converter 52. The digital image signal after A/D conversion is input to the processor device 16.

The processor device 16 includes an image signal acquisition unit 53, a digital signal processor (DSP) 56, a noise reduction unit 58, a memory 61, a signal processing unit 62, and a video signal generation unit 63.

The image signal acquisition unit 53 acquires a digital image signal from the endoscope 12. The DSP 56 performs various kinds of signal processing, such as defect correction processing, offset processing, gain correction processing, linear matrix processing, gamma conversion processing, and demosaic processing, on the image signal acquired by the image signal acquisition unit 53. In the defect correction processing, the signal of a defective pixel of the imaging sensor 48 is corrected. In the offset processing, a dark current component is removed from the image signal subjected to the defect correction processing, and an accurate zero level is set. In the gain correction processing, the signal level is adjusted by multiplying the image signal after the offset processing by a specific gain.

Linear matrix processing for increasing color reproducibility is performed on the image signal after the gain correction processing. Then, the brightness or saturation is adjusted by gamma conversion processing. Demosaic processing (also referred to as isotropic processing or synchronization processing) is performed on the image signal after the gamma conversion processing, and the signal of missing color in each pixel is generated by interpolation. Through the demosaic processing, all pixels have signals of RGB colors. The noise reduction unit 58 reduces noise by performing noise reduction processing on the image signal subjected to the demosaic processing or the like by the DSP 56 using, for example, a moving average method or a median filter method. The image signal from which noise has been reduced is stored in the memory 61.

The signal processing unit 62 acquires the image signal after noise reduction from the memory 61. Then, image processing, such as color conversion processing, color emphasis processing, and structure emphasis processing, is performed on the acquired image signal as necessary, thereby generating a color endoscope image in which the observation target is reflected. The color conversion processing is a process of performing color conversion on the image signal by 3×3 matrix processing, gradation conversion processing, three-dimensional look-up table (LUT) processing, and the like. The color emphasis processing is performed on the image signal after the color conversion processing. The structure emphasis processing is a process of emphasizing a specific tissue or structure included in an observation target, such as a blood vessel or a pit pattern, and is performed on the image signal after the color emphasis processing. Since the endoscope image generated by the signal processing unit 62 is a normal observation image in a case where the observation mode is a normal observation mode and is a special observation image in a case where the observation mode is a special observation mode, the content of the color conversion processing, the color emphasis processing, and the structure emphasis processing differs depending on the observation mode. In the case of the normal observation mode, the signal processing unit 62 generates a normal observation image by performing the above-described various kinds of signal processing by which the observation target has a natural color shade. In the case of the special observation mode, the signal processing unit 62 generates a special observation image by performing the above-described various kinds of signal processing for emphasizing at least a blood vessel of the observation target. In the special observation image generated by the signal processing unit 62, a blood vessel (so-called surface layer blood vessel) located at a relatively shallow position inside the observation target with the mucosal surface as a reference has a magenta type color (for example, brown color), and a blood vessel located at a relatively deep position inside the observation target with the mucosal surface as a reference (so-called middle deep layer blood vessel) has a cyan type color (for example, green color). For this reason, the blood vessel of the observation target is emphasized due to the color difference with respect to the mucous membrane expressed by a pink type color.

The signal processing unit 62 inputs the generated endoscope image to the video signal generation unit 63. The video signal generation unit 63 converts the endoscope image into a video signal to be output and displayed on the monitor 18. In a case where a release instruction is input by operating the still image acquisition instruction unit 13*a*, the signal processing unit 62 stores the generated endoscope image in a storage 64. The storage 64 is an external storage device connected to the processor device 16 through a local area network (LAN). For example, the storage 64 is a file server of a system for filing an endoscope image, such as a picture archiving and communication system (PACS), or a network attached storage (NAS). The endoscope image stored in the storage 64 is used by an image processing apparatus 65.

Figure 3:
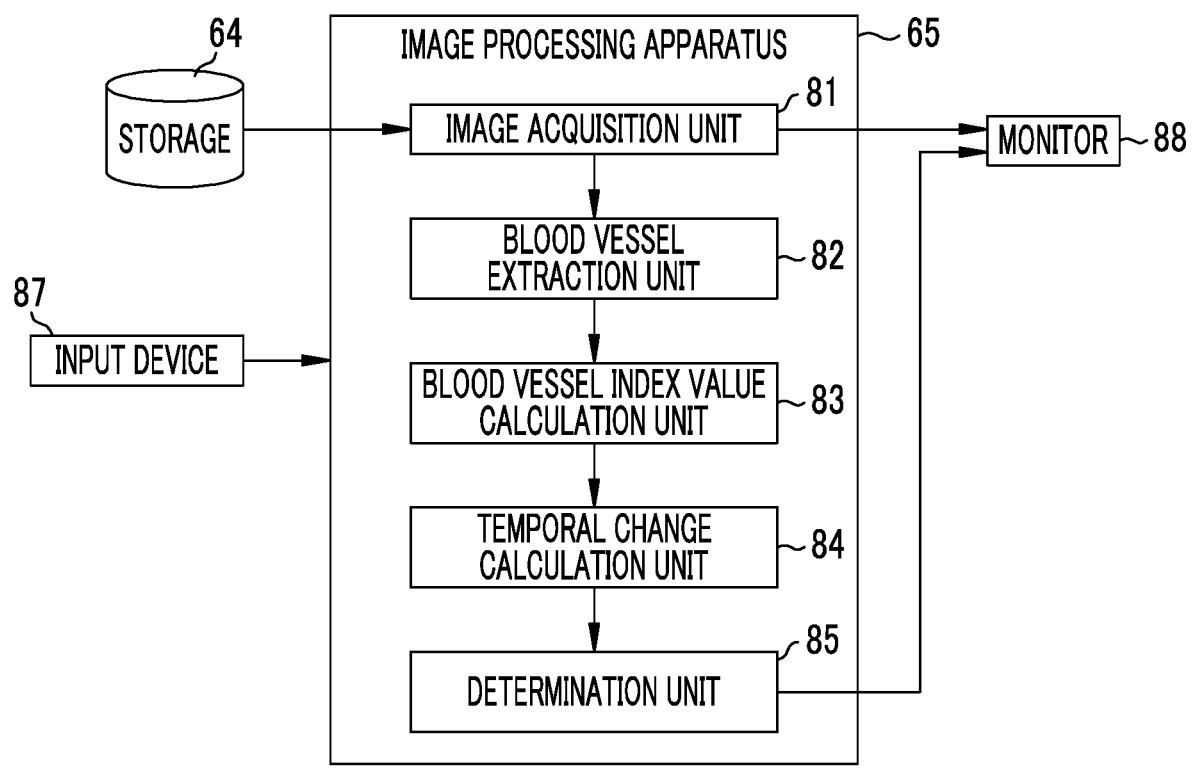
FIG. 3 is a block diagram of an image processing apparatus.

The image processing apparatus 65 is an apparatus that performs image processing on the endoscope image to calculate a blood vessel parameter for diagnostic assistance and calculate a blood vessel change index using the blood vessel parameter. As shown in FIG. 3, the image processing apparatus 65 includes an image acquisition unit 81, a blood vessel extraction unit 82, a blood vessel index value calculation unit 83, a temporal change calculation unit 84, and a determination unit 85. An input device 87 including a keyboard and a pointing device used for designating a region of interest (ROI) or a monitor 88 functioning as a display unit for displaying an endoscope image, a determination result of the determination unit 85, and the like is connected to the image processing apparatus 65.

The image acquisition unit 81 acquires a plurality of endoscope images, which are obtained by imaging the observation target at different times by the endoscope, from the storage 64. Endoscope images stored in the storage 64 include a normal observation image and a special observation image. In the present embodiment, the image acquisition unit 81 acquires a special observation image emphasizing the blood vessel from the storage 64.

Figure 4:
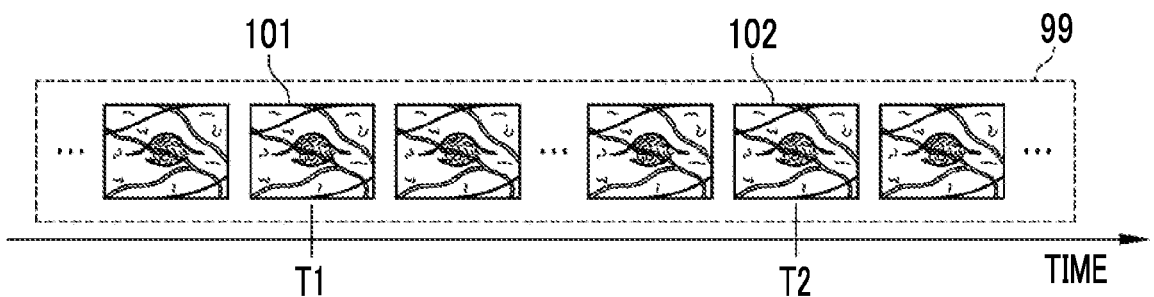
FIG. 4 is an explanatory diagram showing an endoscope image stored in a storage.

As shown in FIG. 4, a plurality of endoscope images 99 obtained by imaging the observation target at different times (different dates and times) are stored in the storage 64. The image acquisition unit 81 acquires a plurality of endoscope images, which are obtained by imaging at different times, from the plurality of endoscope images 99 according to a setting input or the like by the user. In the present embodiment, for the sake of simplicity, a first endoscope image 101 and a second endoscope image 102 are acquired. The first endoscope image 101 is an endoscope image obtained by imaging the observation target earlier than the second endoscope image 102. Conversely, the second endoscope image 102 is an endoscope image obtained by imaging the observation target later than the first endoscope image 101. That is, "first" and "second" indicate the order of the endoscope image acquisition time. Between two endoscope images acquired by the image acquisition unit 81, an endoscope image obtained by imaging the observation target relatively earlier is the first endoscope image 101, and an endoscope image obtained by imaging the observation target relatively later is the second endoscope image 102. In a case where the imaging time T1 of the first endoscope image 101 is compared with the imaging time T2 of the second endoscope image 102, T1<T2 is satisfied.

The blood vessel extraction unit 82 extracts blood vessels of the observation target from each of the plurality of endoscope images acquired by the image acquisition unit 81. The blood vessel extraction method is, for example, frequency filtering. In the present embodiment, since the image acquisition unit 81 acquires the two endoscope images of the first endoscope image 101 and the second endoscope image 102, the blood vessel extraction unit 82 extracts blood vessels of the observation target from each of the first endoscope image 101 and the second endoscope image 102. Hereinafter, the blood vessel extracted from the first endoscope image 101 is referred to as a first blood vessel, and the blood vessel extracted from the second endoscope image 102 is referred to as a second blood vessel. In the present embodiment, the blood vessel extraction unit 82 extracts blood vessels from the entire endoscope image acquired by the image acquisition unit 81. However, in a case where a region of interest is designated, blood vessels may be extracted only within the designated region of interest.

The blood vessel index value calculation unit 83 calculates a blood vessel index value Di for each of the blood vessels extracted from the endoscope image. That is, in the present embodiment, the blood vessel index value calculation unit 83 calculates a first blood vessel index value Di1, which is the blood vessel index value Di of the first endoscope image, using the first blood vessel extracted from the first endoscope image 101, and calculates a second blood vessel index value Di2, which is the blood vessel index value Di of the second endoscope image 102, using the second blood vessel extracted from the second endoscope image 102.

The blood vessel index value Di is an index value relevant to the blood vessel of the observation target, and is an index value that can be used for determination or classification of a lesion. For example, the blood vessel information Vi functions as the blood vessel index value Di. The blood vessel index value Di can also be calculated using the blood vessel information Vi. Therefore, as the blood vessel index value Di, the blood vessel index value calculation unit 83 calculates the blood vessel information Vi or an index value P that is calculated using the blood vessel information Vi. In the present embodiment, since the blood vessel information Vi itself is used as the blood vessel index value Di, the blood vessel index value calculation unit 83 functions as a blood vessel information calculation unit that calculates the blood vessel information Vi.

Specifically, the blood vessel index value calculation unit 83 calculates the first blood vessel index value Di1 and the second blood vessel index value Di2, and these first blood vessel index value Di1 and second blood vessel index value Di2 are blood vessel indices of the same type (for determining or classifying a lesion according to the same reference). The first blood vessel index value Di1 and the second blood vessel index value Di2 are basically different values except for a case where these are the same by chance. The difference between the first blood vessel index value Di1 and the second blood vessel index value Di2 indicates a temporal change of the observation target between the imaging time T1 of the first endoscope image 101 and the imaging time T2 of the second endoscope image 102.

The blood vessel information Vi is, for example, the number of blood vessels, the number of branches, a branching angle, a distance between branch points, the number of crossings, a thickness, a change in thickness, complexity of thickness change, a length, an interval, a depth with respect to a mucous membrane as a reference, a height difference, an inclination, an area, a density, a contrast, a color, color change, degree of meandering, blood concentration, oxygen saturation, proportion of arteries, proportion of veins, concentration of administered coloring agent, a running pattern, or a blood flow rate. These are examples of blood vessel information, and other information regarding blood vessels may be calculated as the blood vessel information.

The number of blood vessels is the number of blood vessels extracted in the entire endoscope image or in a region of interest. The number of blood vessels is calculated using, for example, the number of branch points (the number of branches) of the extracted blood vessel, the number of intersections (the number of crossings) with other blood vessels, and the like. The branching angle of a blood vessel is an angle formed by two blood vessels at a branch point. The distance between branch points is a linear distance between an arbitrary branch point and a branch point adjacent thereto or a length along a blood vessel from an arbitrary branch point to a branch point adjacent thereto.

The number of crossings between blood vessels is the number of intersections at which blood vessels having different submucosal depths cross each other on the endoscope image. More specifically, the number of crossings between blood vessels is the number of blood vessels, which are located at relatively shallow submucosal positions, crossing blood vessels located at deep positions.

The thickness of a blood vessel (blood vessel diameter) is a distance between the blood vessel and the boundary of the mucous membrane. For example, the thickness of a blood vessel (blood vessel diameter) is measured by counting the number of pixels along the lateral direction of the blood vessel from the edge of the extracted blood vessel through the blood vessel. Therefore, the thickness of a blood vessel is the number of pixels. However, in a case where the imaging distance, zoom magnification and the like at the time of capturing an endoscope image are known, the number of pixels can be converted into a unit of length, such as "μm", as necessary.

The change in the thickness of a blood vessel is blood vessel information regarding a variation in the thickness of the blood vessel, and is also referred to as the aperture inconsistency. The change in the thickness of a blood vessel is, for example, a change rate of the blood vessel diameter (also referred to as the degree of expansion). Using the thickness (minimum diameter) of the thinnest portion of the blood vessel and the thickness (maximum diameter) of the thickest portion of the blood vessel, the change rate of the blood vessel diameter is calculated as "blood vessel diameter change rate (%)=minimum diameter/maximum diameter×100".

In a case where an endoscope image obtained by imaging the observation target in a past examination and an endoscope image obtained by imaging the same observation target in a subsequent new examination are used, a temporal change in the thickness of the same blood vessel extracted from the endoscope image obtained by the subsequent new examination with respect to the thickness of the blood vessel extracted from the endoscope image obtained by the past examination may be the change in the thickness of the blood vessel.

As a change in the thickness of the blood vessel, a proportion of a small diameter portion or a proportion of a large diameter portion may be calculated. The small diameter portion is a portion whose thickness is equal to or less than the threshold value, and the large diameter portion is a portion where the thickness is equal to or greater than the threshold value. The proportion of a small diameter portion is calculated as "proportion of small diameter portion (%)=length of small diameter portion/length of blood vessel×100". Similarly, the proportion of a large diameter portion is calculated as "proportion of large diameter portion (%)=length of large diameter portion/length of blood vessel×100".

The complexity of the change in the thickness of a blood vessel (hereinafter, referred to as the "complexity of the thickness change") is blood vessel information indicating how complex the change is in a case where the thickness of the blood vessel changes, and is blood vessel information calculated by combining a plurality of pieces of blood vessel information indicating the change in the thickness of the blood vessel (that is, the change rate of the blood vessel diameter, the proportion of the small diameter portion, or the proportion of the large diameter portion). The complexity of the thickness change can be calculated, for example, by the product of the change rate of the blood vessel diameter and the proportion of the small diameter portion.

The length of a blood vessel is the number of pixels counted along the longitudinal direction of the extracted blood vessel.

The interval between blood vessels is the number of pixels showing the mucous membrane between the edges of the extracted blood vessel. In the case of one extracted blood vessel, the interval between blood vessels has no value.

The depth of a blood vessel is measured with the mucous membrane (more specifically, the mucosal surface) as a reference. The depth of a blood vessel with the mucous membrane as a reference can be calculated based on, for example, the color of the blood vessel. In the case of the special observation image, a blood vessel located near the mucosal surface is expressed by a magenta type color, and a blood vessel far from the mucosal surface and located at a deep submucosal position is expressed by a cyan type color. Therefore, the blood vessel index value calculation unit 83 calculates the depth of the blood vessel with the mucous membrane as a reference for each pixel based on the balance of the signals of the respective colors of R, G, and B of the pixels extracted as a blood vessel.

The height difference of a blood vessel is the magnitude of the difference in the depth of the blood vessel. For example, the height difference of one blood vessel of interest is calculated by the difference between the depth (maximum depth) of the deepest portion of the blood vessel and the depth (minimum depth) of the shallowest portion. In a case where the depth is constant, the height difference is zero.

The inclination of a blood vessel is the change rate of the depth of the blood vessel, and is calculated using the length of the blood vessel and the depth of the blood vessel. That is, the inclination of a blood vessel is calculated as "inclination of blood vessel=depth of blood vessel/length of blood vessel". The blood vessel may be divided into a plurality of sections, and the inclination of the blood vessel may be calculated in each section.

The area of a blood vessel is the number of pixels extracted as a blood vessel or a value proportional to the number of pixels extracted as a blood vessel. The area of a blood vessel is calculated within the region of interest, outside the region of interest, or for the entire endoscope image.

The density of blood vessels is a proportion of blood vessels in a unit area. A region of a specific size (for example, a region of a unit area) including pixels for calculating the density of blood vessels at its approximate center is cut out, and the proportion of blood vessels occupying all the pixels within the region is calculated. By performing this on all the pixels of the region of interest or the entire endoscope image, the density of blood vessels of each pixel can be calculated.

The contrast of a blood vessel is a relative contrast with respect to the mucous membrane of the observation target. The contrast of a blood vessel is calculated as, for example, "$Y_V/Y_M$" or "$(Y_V-Y_M)/(Y_V+Y_M)$", using the brightness $Y_V$ of the blood vessel and the brightness $Y_M$ of the mucous membrane.

The color of a blood vessel is each value of RGB of pixels showing the blood vessel. The change in the color of a blood vessel is a difference or ratio between the maximum value and the minimum value of the RGB values of pixels showing the blood vessel. For example, the ratio between the maximum value and the minimum value of the B value of a pixel showing the blood vessel, the ratio between the maximum value and the minimum value of the G value of a pixel showing the blood vessel, or the ratio between the maximum value and the minimum value of the R value of a pixel showing the blood vessel indicates a change in the color of the blood vessel. Needless to say, conversion into complementary colors may be performed to calculate the color of the blood vessel and a change in the color of the blood vessel for each value of cyan, magenta, yellow, green, and the like.

The degree of meandering of a blood vessel is blood vessel information indicating the size of a range in which the blood vessel travels meandering. The degree of meandering of a blood vessel is, for example, the area (the number of pixels) of a minimum rectangle including the blood vessel for which the degree of meandering is to be calculated. The ratio of the length of the blood vessel to the linear distance between the start point and the end point of the blood vessel may be used as the degree of meandering of the blood vessel.

The blood concentration of a blood vessel is blood vessel information proportional to the amount of hemoglobin contained in a blood vessel. Since the ratio (G/R) of the G value to the R value of a pixel showing a blood vessel is proportional to the amount of hemoglobin, the blood concentration can be calculated for each pixel by calculating the value of G/R.

The oxygen saturation of a blood vessel is the amount of oxygenated hemoglobin to the total amount of hemoglobin (total amount of oxygenated hemoglobin and reduced hemoglobin). The oxygen saturation can be calculated by using an endoscope image obtained by imaging the observation target with light in a specific wavelength range (for example, blue light having a wavelength of about 470±10 nm) having a large difference between the light absorption coefficients of oxygenated hemoglobin and reduced hemoglobin. In a case where blue light having a wavelength of about 470±10 nm is used, the B value of the pixel showing the blood vessel is correlated with the oxygen saturation. Therefore, by using a table or the like that associates the B value with the oxygen saturation, it is possible to calculate the oxygen saturation of each pixel showing the blood vessel.

The proportion of arteries is the ratio of the number of pixels of arteries to the number of pixels of all the blood vessels. Similarly, the proportion of veins is the ratio of the number of pixels of veins to the number of pixels of all the blood vessels. Arteries and veins can be distinguished by oxygen saturation. For example, assuming that a blood vessel having an oxygen saturation of 70% or more is an artery and a blood vessel having an oxygen saturation less than 70% is a vein, extracted blood vessels can be divided into arteries and veins. Therefore, the proportion of arteries and the proportion of veins can be calculated.

The concentration of an administered coloring agent is the concentration of a coloring agent sprayed on the observation target or the concentration of a coloring agent injected into the blood vessel by intravenous injection. The concentration of the administered coloring agent is calculated, for example, by the ratio of the pixel value of the coloring agent color to the pixel value of a pixel other than the coloring agent color. For example, in a case where a coloring agent for coloring in blue is administered, B/G, B/R, and the like indicate the concentration of the coloring agent fixed (or temporarily adhered) to the observation target.

The traveling pattern of a blood vessel is blood vessel information regarding the traveling direction of a blood vessel. The traveling pattern of a blood vessel is, for example, an average angle (traveling direction) of a blood vessel with respect to a reference line arbitrarily set, a dispersion (variation in traveling direction) of an angle formed by a blood vessel with respect to a reference line set arbitrarily, and the like.

The blood flow rate (also referred to as a blood flow speed) of a blood vessel is the number of red blood cells that can pass per unit time. The blood flow rate of the blood vessel can be calculated using the Doppler shift frequency of each pixel showing the blood vessel of the endoscope image, for example, in a case where an ultrasound probe is used together through the forceps channel of the endoscope 12 or the like.

In the present embodiment, the blood vessel index value calculation unit 83 calculates a plurality of kinds of blood vessel information Vi. That is, the blood vessel index value calculation unit 83 calculates a plurality of types first blood vessel index values Di1, and calculates a plurality of types of second blood vessel index values Di2. The plurality of types of first blood vessel index values Di1 and the plurality of types of second blood vessel index values Di2 are configured to have the same elements. For example, the blood vessel index value calculation unit 83 calculates "depth", "thickness", and "density" of the first blood vessel as the first blood vessel index value Di1, and calculates "depth", "thickness", and "density" of the second blood vessel as the second blood vessel index value Di2.

In the image processing apparatus 65, it is possible to set a region of interest in the entirety or a part of the endoscope image by operating the input device 87. For example, in a case where a part of the endoscope image is set as a region of interest, the blood vessel index value calculation unit 83 calculates the blood vessel index value Di (in the present embodiment, the blood vessel information Vi) in the region of interest. In a case where a region of interest is not designated or a case where the entire endoscope image is set as a region of interest, the blood vessel index value calculation unit 83 calculates the blood vessel index value Di by setting the entire endoscope image as a region of interest.

The blood vessel index value calculation unit 83 calculates the blood vessel index value Di for each pixel of the endoscope image. For example, the blood vessel index value Di of one pixel is calculated using the data of pixels in a predetermined range including a pixel whose blood vessel index value Di is to be calculated (for example, a range of 99×99 pixels centered on the pixel whose blood vessel index value Di is to be calculated). For example, in the case of calculating the "thickness of a blood vessel" (blood vessel information Vi) as the blood vessel index value Di, the "thickness of a blood vessel" for each pixel is a statistic of the thickness of a blood vessel in the predetermined range. The statistic is a so-called basic statistic, and is, for example, a maximum value, a minimum value, an average value, a median, or a mode. Needless to say, it is also possible to use statistics other than the exemplified values. For example, a value (ratio between the maximum value and the minimum value or the like) calculated using a so-called representative value, such as the maximum value, the minimum value, the average value, the median, or the mode, or a so-called scattering degree, such as a dispersion, a standard deviation, and a variation coefficient, can be used.

In the case of setting a region of interest, the blood vessel index value calculation unit 83 calculates a statistic of the blood vessel index value Di of each pixel included in the region of interest, and sets the value as the blood vessel index value Di of the region of interest. For example, in the case of calculating the thickness (blood vessel information Vi) of a blood vessel as the blood vessel index value Di, the "thickness of a blood vessel" of each pixel is calculated as described above. In a case where a region of interest is set, a statistic of the "thickness of a blood vessel" of each pixel included in the region of interest is further calculated, and one "thickness of a blood vessel" is calculated for one set region of interest. The same is true for a case where the entire endoscope image is set as a region of interest.

The statistic in the case of calculating a blood vessel index value for each pixel and the statistic in the case of calculating a blood vessel index value of a region of interest may be the same statistic, or may be different. For example, in the case of calculating the thickness of a blood vessel for each pixel, an average value of the thickness of the blood vessel appearing in a "predetermined range" may be calculated. Thereafter, even in the case of calculating the thickness of a blood vessel in the region of interest, the average value of the thickness of the blood vessel of each pixel may be calculated, or a mode of the thickness of the blood vessel of each pixel may be calculated.

In the present embodiment, the blood vessel index value Di is calculated for each pixel as described above and then the statistic of the blood vessel index value Di calculated for each pixel within the region of interest is calculated, thereby calculating the blood vessel information of the region of interest. However, depending on the type of the blood vessel index value Di to be calculated, a relationship between the method of calculating the statistic in the case of calculating the blood vessel index value Di for each pixel and the method of calculating the statistic in the case of calculating the blood vessel information of the region of interest, and the like, it is possible to omit the calculation of the blood vessel index value Di for each pixel. In the case of the "thickness of a blood vessel", an average value of the thickness of the blood vessel appearing in the region of interest can be set as the thickness of the blood vessel in the region of interest.

The temporal change calculation unit 84 calculates a temporal change of the blood vessel index value Di. In the present embodiment, the temporal change calculation unit 84 calculates a temporal change of the second blood vessel index value Di2 with respect to the first blood vessel index value Di1. The "temporal change" of the blood vessel index value Di is a difference $\Delta$ between the first blood vessel index value Di1 and the second blood vessel index value Di2 ($\Delta$=Di2−Di1 or $\Delta$=Di1−Di2), a ratio R between the first blood vessel index value Di1 and the second blood vessel index value Di2 (R=Di2/Di1 or R=Di1/Di2), or a change rate C of the second blood vessel index value Di2 to the first blood vessel index value Di1 (C=(Di2−Di1)/Di1, C=(Di1−Di2)/Di2, or C=(Di2−Di1)/(T2−T1)). Taking the elapsed time into consideration, the difference $\Delta$, the ratio R, or the change rate C per unit time may be used as the temporal change of the blood vessel index value Di. The unit time is 1 year, 1 month, 1 day, 1 hour, 1 minute, 1 second, or the like.

"Calculating the temporal change" of the blood vessel index value Di includes not only actually calculating the difference $\Delta$, the ratio R, or the change rate C but also holding the data of the first blood vessel index value Di and the second blood vessel index value Di in a state in which the difference $\Delta$, the ratio R, or the change rate C can be calculated. "Holding the data of the first blood vessel index value Di and the second blood vessel index value Di in a state in which the difference $\Delta$, the ratio R, or the change rate C can be calculated" refers to, for example, making it possible to generate or display the graph of the blood vessel index value with respect to the imaging time by associating the first blood vessel index value Di1 with the imaging time T1 of the first endoscope image 101 and associating the second blood vessel index value Di2 with the imaging time T2 of the second endoscope image 102.

In the present embodiment, since a plurality of kinds of blood vessel information Vi are calculated as the blood vessel index value Di, the blood vessel index value calculation unit 83 calculates the temporal change of the blood vessel index value Di for each blood vessel information Vi. For example, in the case of calculating three kinds of blood vessel information Vi of "depth", "thickness", and "density" as the first blood vessel index value Di1 and the second blood vessel index value Di2, the temporal change calculation unit 84 calculates the temporal change of "depth", the temporal change of "thickness", and the temporal change of "density".

The determination unit 85 determines (or classifies) the state of the mucous membrane of the observation target using the temporal change of the second blood vessel index value Di2 with respect to the first blood vessel index value Di1. The "state of the mucous membrane" of the observation target is a comprehensive status as the entire mucous membrane including blood vessels. For example, the "state of the mucous membrane" of the observation target is "normal", "adenoma" (suspected of adenoma), "cancer" (suspected of cancer), and the like.

More specifically, the determination unit 85 determines the state of the mucous membrane of the observation target from the difference $\Delta$, the ratio R, or the change rate C between the first blood vessel index value Di1 and the second blood vessel index value Di2. For example, in the case of calculating "depth", "thickness", and "density" as the first blood vessel index value Di1 and the second blood vessel index value Di2, the determination unit 85 determines the state of the mucous membrane of the observation target using the temporal change of "depth", the temporal change of "thickness", and the temporal change of "density". In addition, the determination unit 85 determines the state of the mucous membrane of the observation target by comparing the temporal change of the second blood vessel index value Di2 with respect to the first blood vessel index value Di1 with a threshold value.

The determination unit 85 can perform further calculation using the difference $\Delta$, the ratio R, or the change rate C between the first blood vessel index value Di1 and the second blood vessel index value Di2, and determine the state of the mucous membrane of the observation target according to the calculation result. In the present embodiment, the determination unit 85 determines the state of the mucous membrane of the observation target based on the difference $\Delta$ between the first blood vessel index value Di1 and the second blood vessel index value Di2. In the present embodiment, a threshold value used in a case where the determination unit 85 determines the state of the mucous membrane of the observation target is set in advance. However, instead of using the threshold value set in advance as in the present embodiment, the determination unit 85 can use a statistic, such as an average value of the blood vessel index value Di of each pixel of the first endoscope image 101 or the blood vessel index value Di of each pixel of the second endoscope image 102, as a threshold value in the case of determining the state of the mucous membrane of the observation target. In a case where the statistic of the blood vessel index value Di is used as a threshold value, a threshold value (statistic) is calculated using the blood vessel index value Di of a part or the entirety of the endoscope image. In a case where a region of interest is set, a threshold value (statistic) can be calculated using the blood vessel index value Di in the region of interest or the blood vessel index value Di in a predetermined range around the region of interest. For the calculation of the threshold value, other endoscope images captured between the first endoscope image 101 and the second endoscope image 102 or other endoscope images captured before and after the first endoscope image 101 or the second endoscope image 102 may be used.

Figure 5:
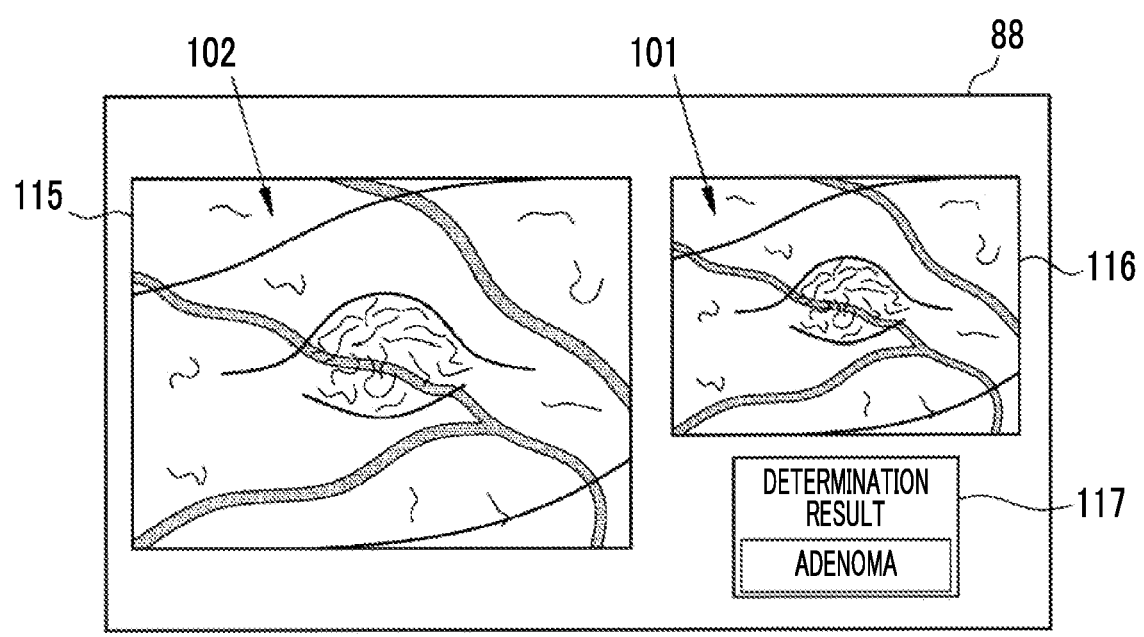
FIG. 5 is a display screen of a monitor.

The image processing apparatus 65 displays the first endoscope image 101 and the second endoscope image 102 acquired by the image acquisition unit 81 and the determination result of the determination unit 85 on the monitor 88. As shown in FIG. 5, the monitor 88 has a main window 115, a subwindow 116, and a determination result display portion 117. The main window 115 and the subwindow 116 display endoscope images, and the determination result display portion 117 displays the determination result of the determination unit 85. The main window 115 is a region for displaying an endoscope image obtained by imaging the observation target relatively later, and the subwindow 116 is a region for displaying an endoscope image obtained by imaging the observation target relatively earlier. Therefore, the image processing apparatus 65 displays the second endoscope image 102 on the main window 115, and displays the first endoscope image 101 on the subwindow 116. In the present embodiment, the main window 115 and the subwindow 116 are provided on the monitor 88. However, the subwindow 116 is not necessarily required. For example, the first endoscope image 101 and the second endoscope image 102 may be switched and displayed on the main window 115 by a user operation or the like.

Figure 6:
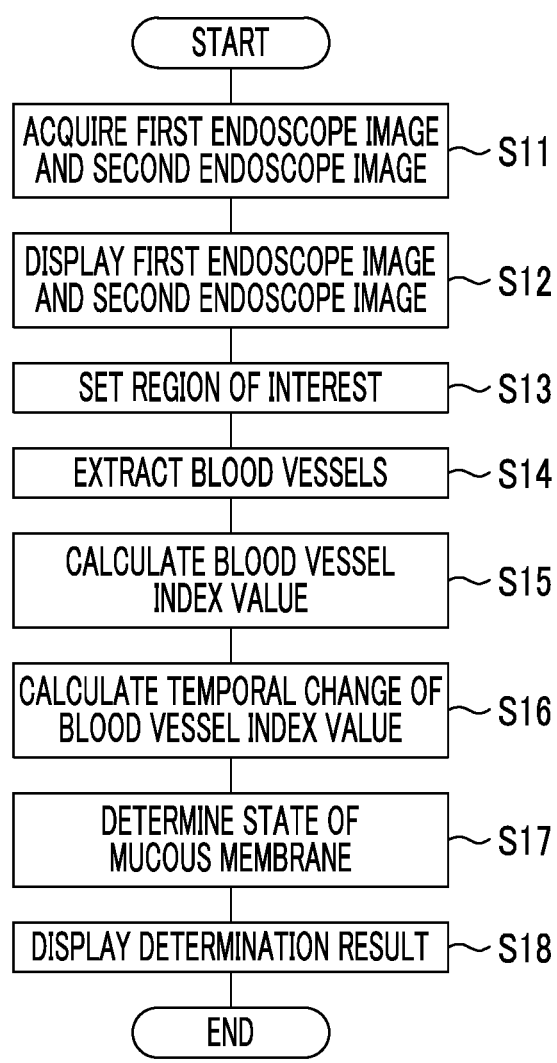
FIG. 6 is a flowchart showing the operation of the image processing apparatus.

Next, the flow of the operation of the image processing apparatus 65 will be described with reference to a flowchart shown in FIG. 6. First, according to the input operation of the input device 87, the image processing apparatus 65 acquires the first endoscope image 101 and the second endoscope image 102 from the storage 64 using the image acquisition unit 81 (S11), and displays these images on the monitor 88 (S12). The image processing apparatus 65 displays the first endoscope image 101 whose imaging time is relatively earlier, between the acquired first endoscope image 101 and second endoscope image 102, on the subwindow 116, and displays the second endoscope image 102 whose imaging time is relatively later on the main window 115.

Figure 7:
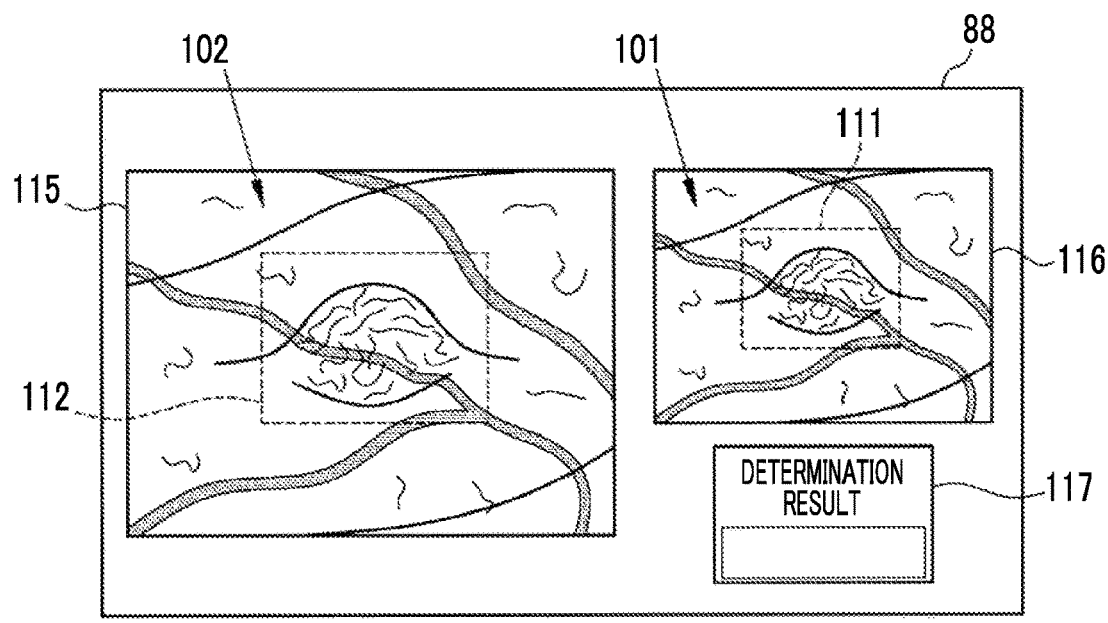
FIG. 7 is an explanatory diagram showing a method of setting a region of interest.

In a case where the selected first endoscope image 101 and second endoscope image 102 are displayed on the monitor 88, a doctor operates the input device 87 to set a region of interest in each of the first endoscope image 101 and the second endoscope image 102 (S13). For example, as shown in FIG. 7, there is an attention portion, which requires diagnosis of whether or not there is a lesion (or the degree of progress of a lesion or the like), in the vicinity of the approximate center of the second endoscope image 102 of the main window 115. Therefore, the doctor operates the input device 87 to set a region of interest (hereinafter, referred to as a second region of interest) 112 including the attention portion in the second endoscope image 102. For the first endoscope image 101 of the subwindow 116, a region of interest (hereinafter, referred to as a first region of interest) 111 including an attention portion, which is the same as (or corresponds to) the attention portion of the second endoscope image 102, is set.

Figure 8:
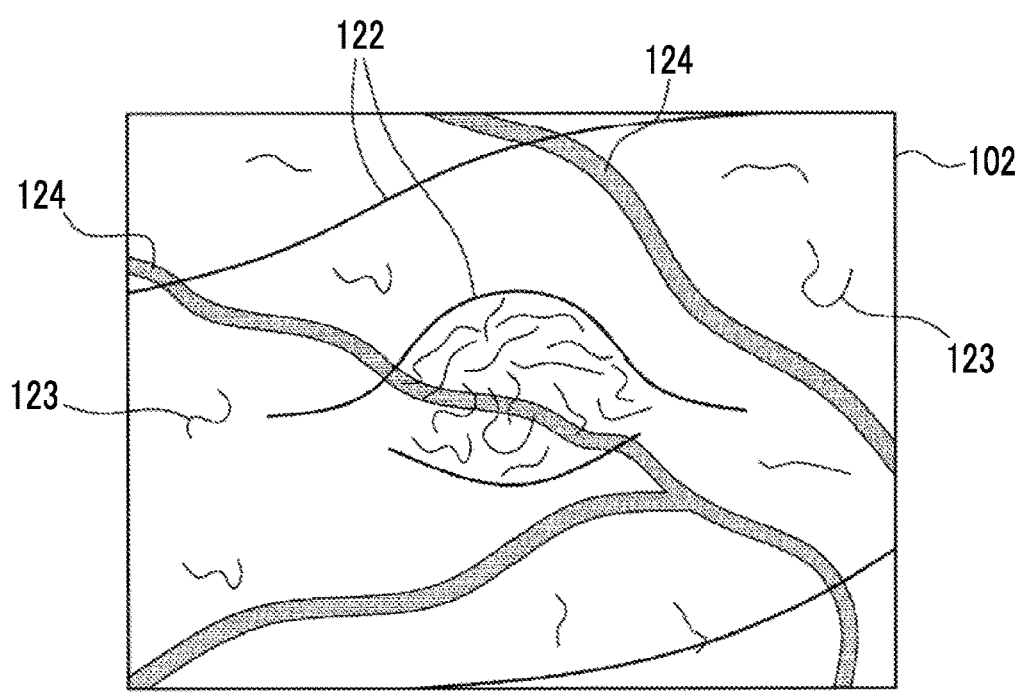
FIG. 8 is a schematic diagram of a second endoscope image.
Figure 9:
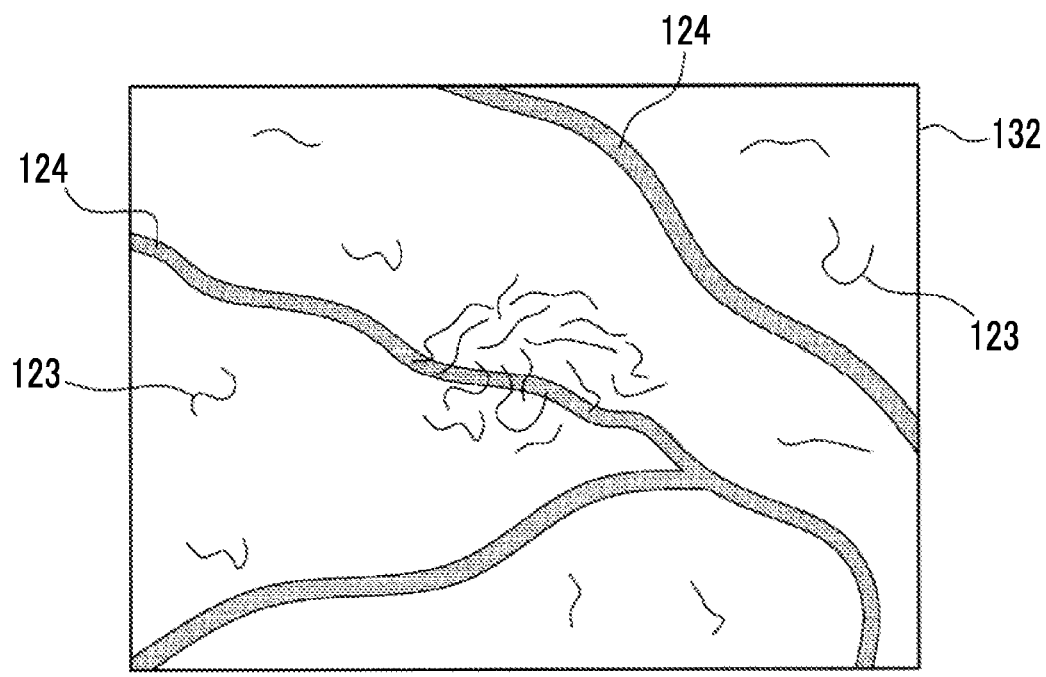
FIG. 9 is a second blood vessel image showing an extracted second blood vessel.

On the other hand, the blood vessel extraction unit 82 extracts the first blood vessel from the first endoscope image 101, and extracts the second blood vessel from the second endoscope image 102 (S14). As shown in FIG. 8, the second endoscope image 102 is a special observation image in which blood vessels are emphasized by color. For example, not only can the shape 122 of the mucosal surface of the observation target be observed, but also a thin surface layer blood vessel 123 located relatively close to the mucosal surface is expressed by a magenta type color and a thick middle deep layer blood vessel 124 located at a relatively deep position under the mucous membrane is expressed by a cyan type color so as to be emphasized. In the case of the second endoscope image 102, the blood vessel extraction unit 82 extracts the surface layer blood vessel 123 and the middle deep layer blood vessel 124 as second blood vessels like a second blood vessel image 132 schematically shown in FIG. 9. The blood vessel extraction unit 82 extracts a first blood vessel from the first endoscope image 101 in the same manner as in the extraction of the second blood vessel from the second endoscope image 102.

In a case where the first blood vessel is extracted from the first endoscope image 101 by the blood vessel extraction unit 82 as described above, the blood vessel index value calculation unit 83 calculates a plurality of kinds of blood vessel information Vi such as "depth", "thickness", and "density" of the first blood vessel for each pixel and further calculates the statistic of the first region of interest 111, thereby calculating a plurality of types of first blood vessel index values Di1 in the first region of interest 111 (S15). Similarly, in a case where the second blood vessel is extracted from the second endoscope image 102 by the blood vessel extraction unit 82, the blood vessel index value calculation unit 83 calculates a plurality of kinds of blood vessel information Vi such as "depth", "thickness", and "density" of the second blood vessel for each pixel and further calculates the statistic of the second region of interest 112, thereby calculating a plurality of types of second blood vessel index values Di2 in the second region of interest 112 (S15).

In a case where the first blood vessel index value Di1 and the second blood vessel index value Di2 are calculated by the blood vessel index value calculation unit 83, the temporal change calculation unit 84 calculates temporal changes of the blood vessel index values (S16). Specifically, the blood vessel index value calculation unit 83 calculates a difference between the depth of the first blood vessel and the depth of the second blood vessel, a difference between the thickness of the first blood vessel and the thickness of the second blood vessel, a difference between the density of the first blood vessel and the density of the second blood vessel, and the like using the depth, thickness, density, and the like (first blood vessel index value Di1) of the first blood vessel and the depth, thickness, density, and the like (second blood vessel index value Di2) of the second blood vessel.

Thereafter, the determination unit 85 determines the state of the mucous membrane of the observation target to be "normal", "adenoma", "cancer", or the like using the difference between the depth of the first blood vessel and the depth of the second blood vessel, the difference between the thickness of the first blood vessel and the thickness of the second blood vessel, the difference between the density of the first blood vessel and the density of the second blood vessel, and the like calculated by the blood vessel index value calculation unit 83 (S17). The image processing apparatus 65 displays the determination result of the determination unit 85 in the determination result display portion 117 of the monitor 88 (refer to S18 and FIG. 5).

As described above, the image processing apparatus 65 automatically performs those other than the selection of the first endoscope image 101 and the second endoscope image 102 and the setting of the first region of interest 111 and the second region of interest 112. For this reason, in a case where the doctor using the image processing apparatus 65 selects two endoscope images from the storage 64 and sets a region of interest in each of the selected endoscope images on the monitor 88, a determination result regarding the state of the mucous membrane of the observation target is automatically displayed in the determination result display portion 117. Since the doctor can immediately grasp the type of lesion suspected or the like by observing the determination result, for example, it is possible to perform diagnosis more directly and efficiently than in a case where the blood vessel index value Di or the blood vessel information Vi is displayed. That is, the image processing apparatus 65 can assist diagnosis more directly and effectively than conventional endoscope systems and the like.

In particular, the image processing apparatus 65 determines the state of the mucous membrane of the observation target from an unprecedented viewpoint called the temporal change of the blood vessel index value Di, Therefore, direct and effective diagnostic assistance can be provided even in a situation where it is difficult to perform definitive diagnosis only with the absolute value of the blood vessel index value Di (temporary value of the blood vessel index value Di).

In the first embodiment described above, the blood vessel index value calculation unit 83 calculates a plurality of kinds of blood vessel information Vi as the blood vessel index value Di. However, depending on the type of lesion or the like, there is a case where it is possible to make a determination by the temporal change of one kind of blood vessel information Vi. Therefore, the blood vessel index value calculation unit 83 may calculate one kind of blood vessel information Vi as the blood vessel index value Di.

Second Embodiment

Figure 10:
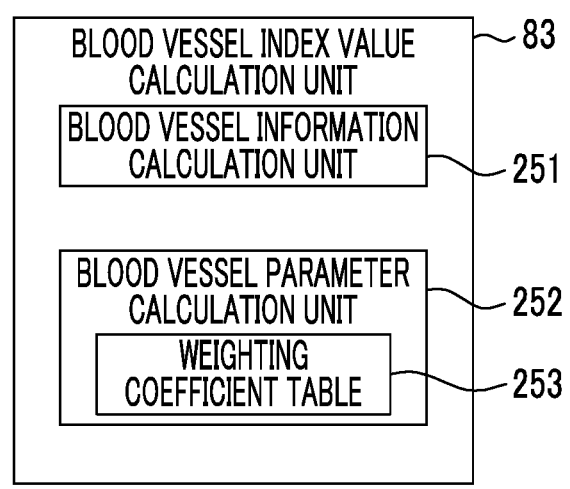
FIG. 10 is a block diagram of a blood vessel index value calculation unit of a second embodiment.

In the first embodiment described above, the blood vessel index value calculation unit 83 calculates the blood vessel information Vi as the blood vessel index value Di. However, an index value (hereinafter, referred to as a blood vessel parameter) P calculated using the blood vessel information Vi may be set as the blood vessel index value Di as described above. In this case, for example, as shown in FIG. 10, a blood vessel information calculation unit 251 and a blood vessel parameter calculation unit 252 are provided in the blood vessel index value calculation unit 83.

Similarly to the blood vessel index value calculation unit 83 of the first embodiment described above, the blood vessel information calculation unit 251 calculates a plurality of kinds of blood vessel information Vi regarding the blood vessel extracted by the blood vessel extraction unit 82. More specifically, the blood vessel information Vi such as "depth", "thickness", and "density" of the first blood vessel extracted from the first endoscope image 101 is calculated, and the blood vessel information Vi such as "depth", "thickness", and "density" of the second blood vessel extracted from the second endoscope image 102 is calculated. That is, the blood vessel information calculation unit 251 calculates a plurality of pieces of blood vessel information Vi of the same kind (combination) for each of the first blood vessel and the second blood vessel.

The blood vessel parameter calculation unit 252 calculates an evaluation value called a blood vessel parameter by performing calculation using a plurality of pieces of blood vessel information Vi calculated by the blood vessel information calculation unit 251. Specifically, the blood vessel parameter calculation unit 252 calculates a blood vessel parameter P1 relevant to the first blood vessel by performing calculation using a plurality of kinds of blood vessel information Vi regarding the first blood vessel. In addition, the blood vessel parameter calculation unit 252 calculates a blood vessel parameter P2 relevant to the second blood vessel by performing calculation using a plurality of kinds of blood vessel information Vi regarding the second blood vessel.

The blood vessel parameter calculation unit 252 calculates the blood vessel parameter P1 by multiplying each of the plurality of kinds of blood vessel information Vi regarding the first blood vessel by a weighting coefficient and taking a sum thereof. The weighting coefficient is stored in a weighting coefficient table 253, and is determined in advance, for example, by machine learning. The calculation for calculating the blood vessel parameter P2 using a plurality of kinds of blood vessel information Vi regarding the second blood vessel is the same as the calculation for calculating the blood vessel parameter P1, and the weighting coefficient to be used is also the weighting coefficient table 253 used for the calculation of the blood vessel parameter P1.

The blood vessel parameter P1 regarding the first blood vessel and the blood vessel parameter P2 regarding the second blood vessel are evaluation values for evaluating the state of the blood vessel of the observation target using the same method (by the same calculation). Needless to say, the values of the blood vessel parameter P1 and the blood vessel parameter P2 are basically different values unless the values of the blood vessel parameter P1 and the blood vessel parameter P2 match each other by chance. The difference between the values of the blood vessel parameter P1 and the blood vessel parameter P2 reflects a difference between the imaging time T1 of the first endoscope image 101 and the imaging time T2 of the second endoscope image 102.

In the present embodiment, the blood vessel parameter calculation unit 252 calculates the weighted sum of a plurality of pieces of blood vessel information Vi as the blood vessel parameters P1 and P2 as described above. However, the method of calculating the blood vessel parameters P1 and P2 is arbitrary. For example, the blood vessel parameters P1 and P2 may be calculated by operation including addition, subtraction, multiplication, and division instead of simply taking a weighted sum, or the blood vessel parameters may be calculated using other functions.

Since the blood vessel parameters P1 and P2 are calculated by adding pieces of blood vessel information Vi having different dimensions (units) or the like, the blood vessel parameters P1 and P2 have no physical meaning but function as indices of diagnosis. That is, unlike the blood vessel information Vi, the blood vessel parameters P1 and P2 are values having no physical meaning.

The blood vessel parameters P1 and P2 calculated as described above are suitable as the first blood vessel index value Di1 and the second blood vessel index value Di2, respectively. In a case where the blood vessel parameters P1 and P2 are used as the first blood vessel index value Di1 and the second blood vessel index value Di2, the temporal change calculation unit 84 calculates the difference Δ or the ratio R between the blood vessel parameter P1 and the blood vessel parameter P2 or the change rate C of the blood vessel parameter P2 with respect to the blood vessel parameter P1: Then, the determination unit 85 determines the state of the mucous membrane of the observation target based on the difference Δ or the ratio R between the blood vessel parameter P1 and the blood vessel parameter P2 or the change rate C of the blood vessel parameter P2 with respect to the blood vessel parameter P1.

By determining the state of the mucous membrane based on the temporal change of the blood vessel parameters P1 and P2 as in the present embodiment, the state of the mucous membrane can be determined more accurately than in the case of determining the state of the mucous membrane based on the temporal change of the blood vessel information Vi.

Third Embodiment

Figure 11:
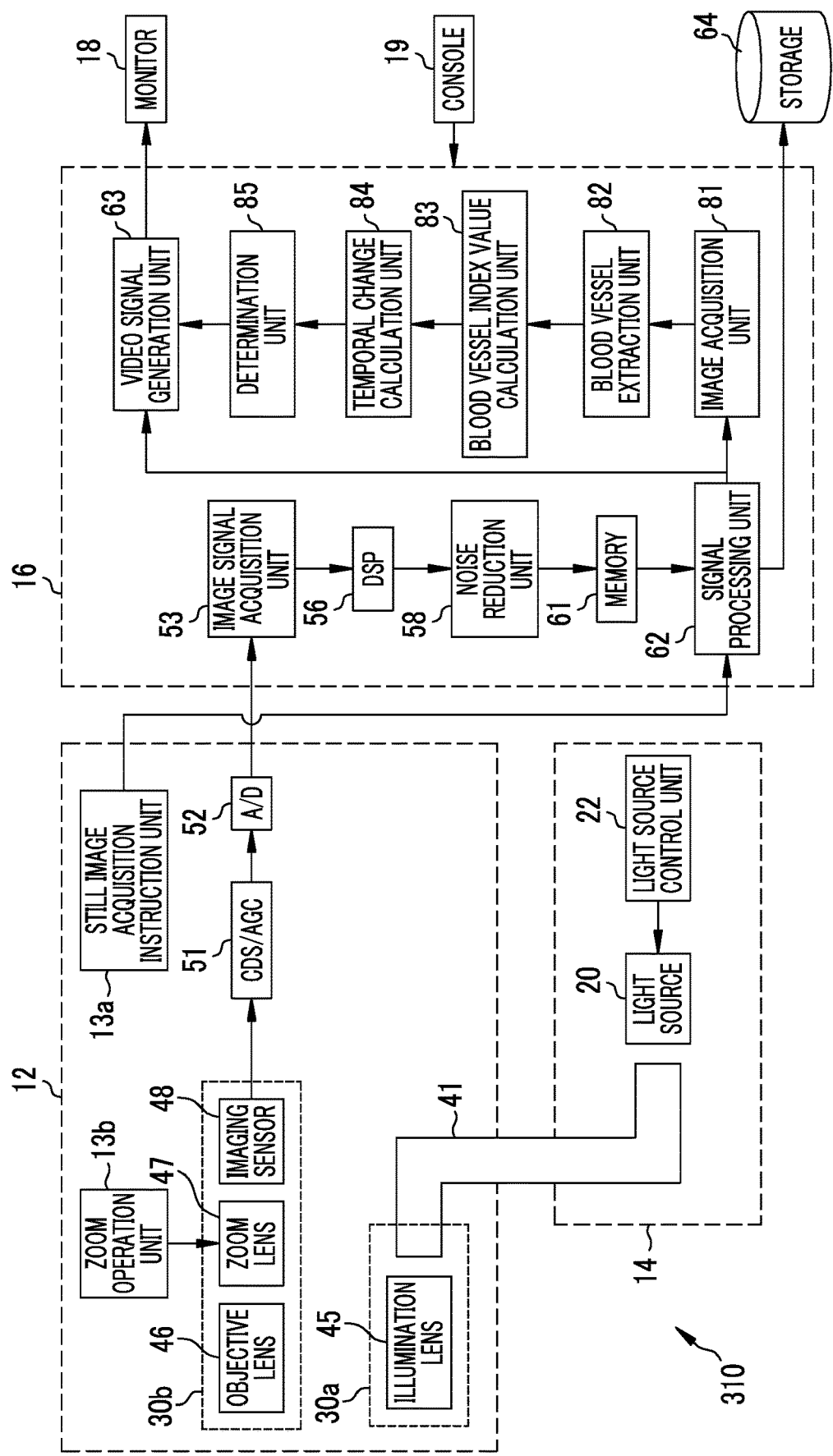
FIG. 11 is a block diagram of an endoscope system of a third embodiment.

In the first and second embodiments described above, the endoscope system 10 stores an endoscope image in the storage 64, and the image processing apparatus 65 acquires the endoscope image from the storage 64 later to calculate a blood vessel parameter. However, the endoscope system 10 may determine the state of the mucous membrane almost in real time while observing the observation target. In this case, as in an endoscope system 310 shown in FIG. 11, the image acquisition unit 81, the blood vessel extraction unit 82, the blood vessel index value calculation unit 83, the temporal change calculation unit 84, and the determination unit 85 are provided in the processor device 16. The configuration of the endoscope 12 or the light source device 14 is the same as that of the endoscope system 10 of the first embodiment.

In a case where each unit of the image processing apparatus 65 is provided in the processor device 16 as described above, the image acquisition unit 81 can directly acquire the endoscope image generated by the signal processing unit 62 from the signal processing unit 62 without passing through the storage 64. Therefore, the image acquisition unit 81 temporarily holds at least two or more endoscope images generated in a case where, for example, a still image acquisition instruction is input, and inputs the endoscope images to the blood vessel extraction unit 82 as the first endoscope image 101 and the second endoscope image 102 of the first embodiment.

As in the case of using the input device 87 in the first embodiment, which endoscope images among the plurality of endoscope images temporarily held by the image acquisition unit 81 are to be used as the first endoscope image 101 and the second endoscope image 102 of the first embodiment can be selected by the doctor using the console 19 of the endoscope system 310. In addition, endoscope images to be used as the first endoscope image 101 and the second endoscope image 102 can be set in advance by using the console 19. For example, among the plurality of endoscope images temporarily held by the image acquisition unit 81, the oldest endoscope image (endoscope image having the earliest imaging time) can be used as the first endoscope image 101, and the newest endoscope image (endoscope image having the latest imaging time) can be used as the second endoscope image 102. The newest endoscope image can be used as the second endoscope image 102, and an endoscope image captured before the predetermined time τ with the imaging time T2 as a reference can be used as the first endoscope image 101.

The operations of the blood vessel extraction unit 82, the blood vessel index value calculation unit 83, the temporal change calculation unit 84, and the determination unit 85 other than the image acquisition unit 81 are the same as those in the endoscope system 10 of the first embodiment. The evaluation result of the determination unit 85 is displayed on the monitor 18 of the endoscope system 310 through the video signal generation unit 63. The display method of the determination result is the same as that in the first embodiment.

As described above, in a case where each unit of the image processing apparatus 65 is provided in the processor device 16, the processor device 16 also functions as the image processing apparatus 65. Therefore, in the endoscope system 310, since the state of the mucous membrane is determined while observing the observation target, it is possible to assist the diagnosis almost in real time. The endoscope system 310 is suitable for observing the effect in the case of administering a medicine to the observation target or performing an operation on the observation target.

In the third embodiment described above, the image acquisition unit 81 directly acquires the endoscope image generated by the signal processing unit 62. However, instead of directly acquiring the endoscope image from the signal processing unit 62, the first endoscope image 101 and the second endoscope image 102 may be acquired from the storage 64 as in the first embodiment or the like. In particular, as the first endoscope image 101, an endoscope image obtained by the past examination that is stored in the storage 64 may be used. In a case where an endoscope image obtained by the past examination is used as the first endoscope image 101, it is possible to know the change of the state of the mucous membrane of the current observation target with respect to the state of the mucous membrane of the past observation target in real time during the current examination.

In the third embodiment described above, the endoscope image that the image acquisition unit 81 acquires from the signal processing unit 62 is an endoscope image generated in a case where a still image acquisition instruction is input. However, the state of the mucous membrane may be determined regardless of the still image acquisition instruction. In this case, it is preferable that the setting of a region of interest, extraction of a blood vessel, calculation of the blood vessel index value Di, calculation of the temporal change of the blood vessel index value Di, and determination of the state of the mucous membrane are automatically performed at predetermined time intervals. The time interval for determining the state of the mucous membrane can be arbitrarily set by the doctor.

Fourth Embodiment

In the first to third embodiments described above, the state of the mucous membrane of the observation target is determined using two endoscope images of the first endoscope image 101 and the second endoscope image 102. However, the state of the mucous membrane of the observation target may be determined using three or more endoscope images.

Figure 12:
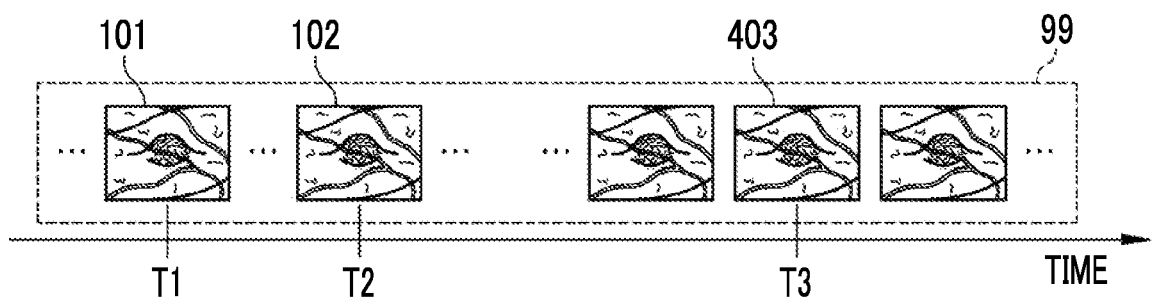
FIG. 12 is an explanatory diagram showing a third endoscope image used in a fourth embodiment.

For example, as shown in FIG. 12, the image acquisition unit 81 acquires not only the first endoscope image 101 and the second endoscope image 102 but also a third endoscope image 403, which is obtained by imaging the observation target after the second endoscope image 102, among the plurality of endoscope images 99 stored in the storage 64. In a case where the imaging time T1 of the first endoscope image 101, the imaging time T2 of the second endoscope image 102, and the imaging time T3 of the third endoscope image 403 are compared, T1<T2<T3 is satisfied.

Figure 13:
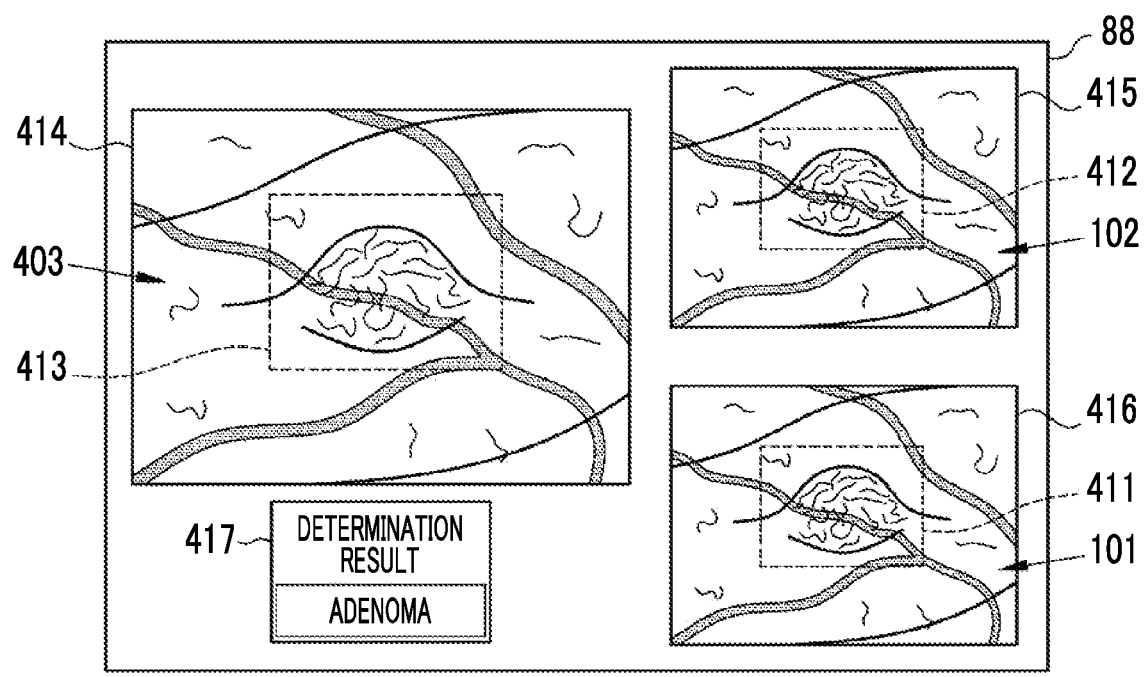
FIG. 13 is a display screen of a monitor in the fourth embodiment.

In this case, as shown in FIG. 13, display regions of three endoscope images of a main window 414, a first subwindow 415, and a second subwindow 416 are provided on the monitor 88. Then, in a case where the image acquisition unit 81 acquires the first endoscope image 101, the second endoscope image 102, and the third endoscope image 403, the image processing apparatus 65 displays the third endoscope image 403 obtained by imaging the observation target relatively most recently in the main window 414, displays the second endoscope image 102 obtained by secondly imaging the observation target in the first subwindow 415, and displays the first endoscope image 101 obtained by imaging the observation target relatively earliest in the second subwindow 416.

In a case where the image processing apparatus 65 displays the first endoscope image 101, the second endoscope image 102, and the third endoscope image 403 on the monitor 88, the doctor sets a region of interest corresponding to each of the endoscope images in the same manner as in the first embodiment and the like. That is, first, a region of interest (hereinafter, referred to as a third region of interest) 413 is set in the third endoscope image 403, and a second region of interest 412 including an attention portion, which is the same as (or corresponds to) the attention portion included in the third region of interest 413, is set in the second endoscope image 102. Similarly for the first endoscope image 101, the first region of interest 411 is set.

In a case where a region of interest is set in each of the first endoscope image 101, the second endoscope image 102, and the third endoscope image 403 as described above, the blood vessel extraction unit 82 extracts a first blood vessel from the first endoscope image 101 and extracts a second blood vessel from the second endoscope image 102. Then, a blood vessel of the observation target is extracted from the third endoscope image 403 in the same manner as extracting the first blood vessel from the first endoscope image 101 and extracting the second blood vessel from the second endoscope image 102. Hereinafter, the blood vessel extracted from the third endoscope image 403 is referred to as a third blood vessel.

Then, the blood vessel index value calculation unit 83 calculates a plurality of kinds of blood vessel information Vi regarding the first blood vessel as the first blood vessel index value Di1, calculates a plurality of kinds of blood vessel information Vi regarding the second blood vessel as the second blood vessel index value Di2, and calculates a plurality of kinds of blood vessel information Vi regarding the third blood vessel as a third blood vessel index value Di3. The plurality of pieces of first blood vessel information, the plurality of pieces of second blood vessel information, and the plurality of pieces of third blood vessel information newly calculated in the present embodiment are the same in kind (combination of kinds).

The temporal change calculation unit 84 calculates the temporal change of the blood vessel index value in a plurality of time sections, and the determination unit 85 determines the state of the mucous membrane of the observation target based on a combination of temporal changes of the blood vessel index values in the plurality of time sections. In the present embodiment, the plurality of time sections are two sections of a section from the imaging time T1 of the first endoscope image 101 to the imaging time T2 of the second endoscope image 102 and a section from the imaging time T2 of the second endoscope image 102 to the imaging time T3 of the third endoscope image 103. Accordingly, the temporal change calculation unit 84 calculates the temporal change of the second blood vessel index value Di2 with respect to the first blood vessel index value Di1 and the temporal change of the third blood vessel index value Di3 with respect to the second blood vessel index value Di2. Then, the determination unit 85 determines the state of the mucous membrane of the observation target based on the combination of the temporal change of the second blood vessel index value Di2 with respect to the first blood vessel index value Di1 and the temporal change of the third blood vessel index value Di3 with respect to the second blood vessel index value Di2.

Figure 14:
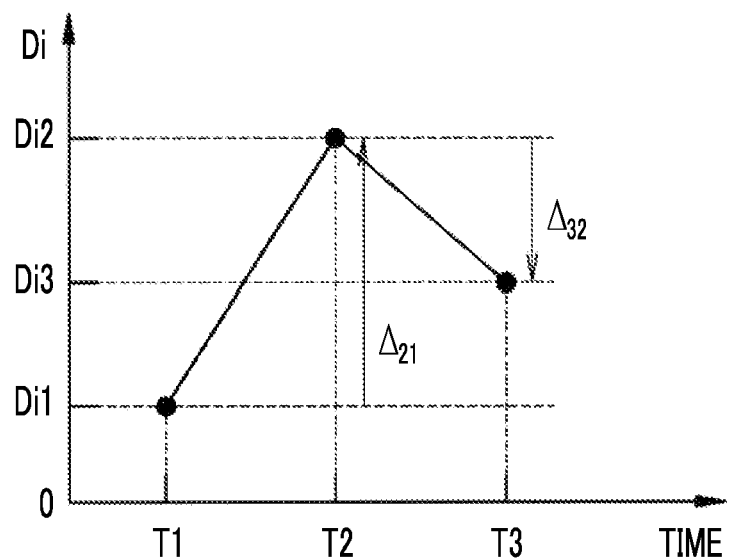
FIG. 14 is a graph showing the temporal changes of first to third blood vessel index values.

For example, as shown in FIG. 14, in a case where a difference $\Delta_{21}$ between the first blood vessel index value Di1 and the second blood vessel index value Di2 and a difference $\Delta_{32}$ between the second blood vessel index value Di2 and the third blood vessel index value Di3 are calculated by the temporal change calculation unit 84, the determination unit 85 determines the state of the mucous membrane of the observation target to be "normal", "adenoma", "cancer", or the like based on the sign or absolute value of the difference $\Delta_{21}$ and the sign or absolute value of the difference $\Delta_{32}$. More specifically, in a case where the difference $\Delta_{21}$ is positive and the difference $\Delta_{32}$ is negative, the state of the mucous membrane of the observation target is determined to be "adenoma" or the like.

In a case where the state of the mucous membrane of the observation target is determined using three or more endoscope images as described above, the state of the mucous membrane of the observation target can be determined more accurately than in a case where only two endoscope images of the first endoscope image 101 and the second endoscope image 102 are used.

Although three endoscope images are used in the fourth embodiment described above, the same is true for a case where four or more endoscope images are used. The same is true for a case where the blood vessel parameter is used as the blood vessel index value Di as in the second embodiment.

In the fourth embodiment described above, the determination unit 85 determines the state of the mucous membrane based on the combination of the temporal change of the second blood vessel index value Di2 with respect to the first blood vessel index value Di1 and the temporal change of the third blood vessel index value Di3 with respect to the second blood vessel index value Di2. However, the determination unit 85 may determine the state of the mucous membrane by combining the values of the first blood vessel index value Di1, the second blood vessel index value Di2, and the third blood vessel index value Di3.

In the fourth embodiment described above, the temporal change calculation unit 84 calculates the temporal change of the second blood vessel index value Di2 with respect to the first blood vessel index value Di1 and the temporal change of the third blood vessel index value Di3 with respect to the second blood vessel index value Di2. However, the temporal change calculation unit 84 may calculate the temporal change of the second blood vessel index value Di2 with respect to the first blood vessel index value Di1 and the temporal change of the third blood vessel index value Di3 with respect to the first blood vessel index value Di1. In addition, the temporal change of the first blood vessel index value Di1 with respect to the second blood vessel index value Di2 and the temporal change of the third blood vessel index value Di3 with respect to the second blood vessel index value Di2 may be calculated. Since they all show the temporal change of substantially the same blood vessel index value Di, the determination unit 85 can determine the state of the mucous membrane of the observation target as in the fourth embodiment described above.

Figure 15:
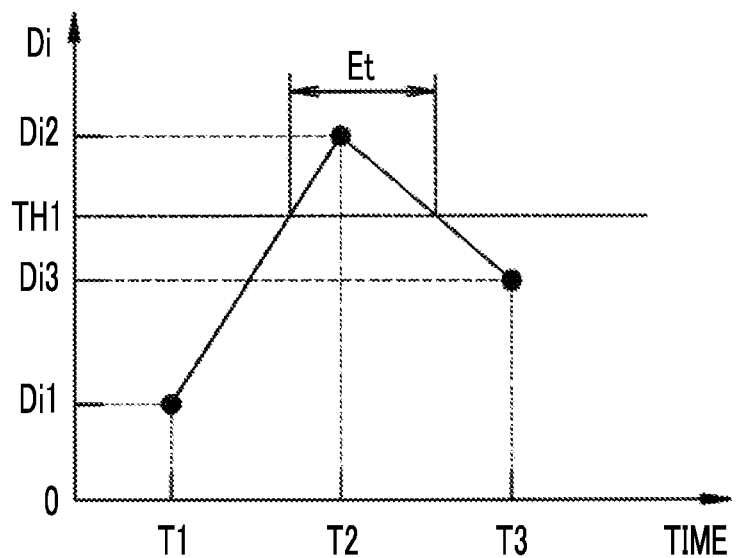
FIG. 15 is a graph showing a period Et during which a blood vessel index value satisfies specific conditions.

The determination unit 85 can determine the state of the mucous membrane using a method different from the above. For example, as shown in FIG. 15, the temporal change of the blood vessel index value Di from the first blood vessel index value Di1 to the third blood vessel index value Di3 is compared with a first threshold value TH1, and the length of a period Et during which the blood vessel index value Di is equal to or greater than the first threshold value TH1 (or equal to or less than the first threshold value TH1, or greater than the first threshold value TH1, or less than the first threshold value TH1) is calculated. Then, the determination unit 85 determines the state of the mucous membrane of the observation target based on the calculated length of the period Et. For example, the state of the mucous membrane of the observation target can be determined by dividing cases into a case where the calculated period Et is zero, a case where the period Et is equal to or greater than a second threshold value TH2, and a case where the period Et is less than the second threshold value TH2. Thus, the method of determining the state of the mucous membrane of the observation target based on the length of the period Et during which the blood vessel index value Di satisfies the determined conditions is particularly suitable for a case where three or more endoscope images are used as in the fourth embodiment described above, but is also suitable for a case where two endoscope images are used as in the first to third embodiments.

Figure 16:
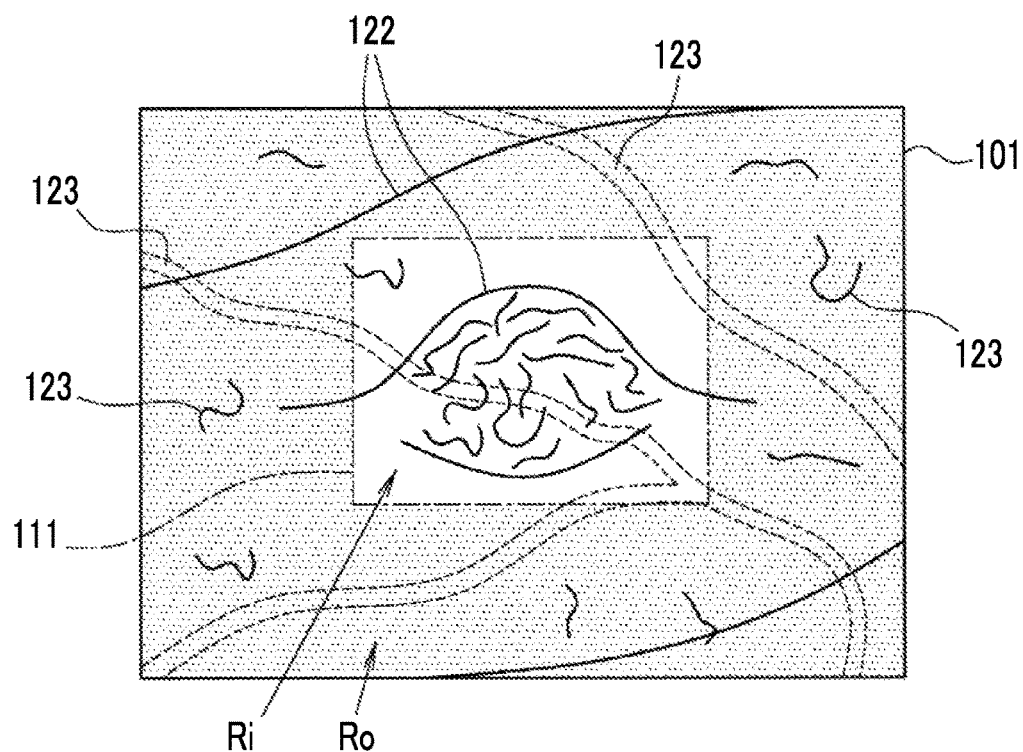
FIG. 16 is an explanatory diagram showing regions inside and outside a region of interest.

In the first to fourth embodiments described above, in a case where the region of interest 111 and the region of interest 112 are set, the blood vessel index value Di is calculated in the region of interest 111 and the region of interest 112, and the state of the mucous membrane is determined based on the temporal change. However, it is preferable that the blood vessel index value calculation unit 83 calculates a blood vessel index value di of a region other than the region of interest 111 and the region of interest 112 in addition to the blood vessel index value Di of the region of interest 111 and the region of interest 112 and determines the state of the mucous membrane of the observation target in consideration of the blood vessel index value di of the region other than the region of interest 111 and the region of interest 112. For example, the blood vessel index value calculation unit 83 calculates not only the first blood vessel index value Di1 of a region Ri in the region of interest 111 of the first endoscope image 101 shown in FIG. 16 but also a first blood vessel index value di1 for a region Ro, to which hatching is applied for the sake of convenience, outside the region of interest 111. Similarly, the blood vessel index value calculation unit 83 calculates not only the second blood vessel index value Di2 of a region in the region of interest 112 of the second endoscope image 102 but also a second blood vessel index value di2 for a region outside the region of interest 112.

The temporal change calculation unit 84 calculates a "spatial change of the blood vessel index value" using the blood vessel index values Di and di of the inside and outside of the region of interest 111 and the region of interest 112, and further calculates a temporal change of the "spatial change of the blood vessel index value".

Specifically, the temporal change calculation unit 84 calculates a difference, a ratio, or a change rate between the first blood vessel index values Di1 and di1 of the inside and outside of the region of interest 111, and calculates a difference, a ratio, or a change rate between the second blood vessel index values Di2 and di2 of the inside and outside of the region of interest 112. The difference, the ratio, or the change rate between the first blood vessel index values Di1 and di1 of the inside and outside of the region of interest 111 is a "spatial change of the blood vessel index value" S1 relevant to the first endoscope image 101. Similarly, the difference, the ratio, or the change rate between the second blood vessel index values Di2 and di2 of the inside and outside of the region of interest 112 is a "spatial change of the blood vessel index value" S2 relevant to the second endoscope image 102.

In a case where the spatial change of the blood vessel index value is calculated as described above, the temporal change calculation unit 84 calculates a temporal change of the "spatial change of the blood vessel index value". That is, a difference, a ratio, or a change rate between the two spatial changes S1 and S2 is calculated. The difference, the ratio, or the change rate between the two spatial changes S1 and S2 is a temporal change γ of the "spatial change of the blood vessel index value". The determination unit 85 determines the state of the mucous membrane of the observation target based on the temporal change γ of the "spatial change of the blood vessel index value". In this manner, the influence of the individual difference of the observation target on the determination result is reduced. As a result, a more accurate determination result is obtained.

Figure 17:
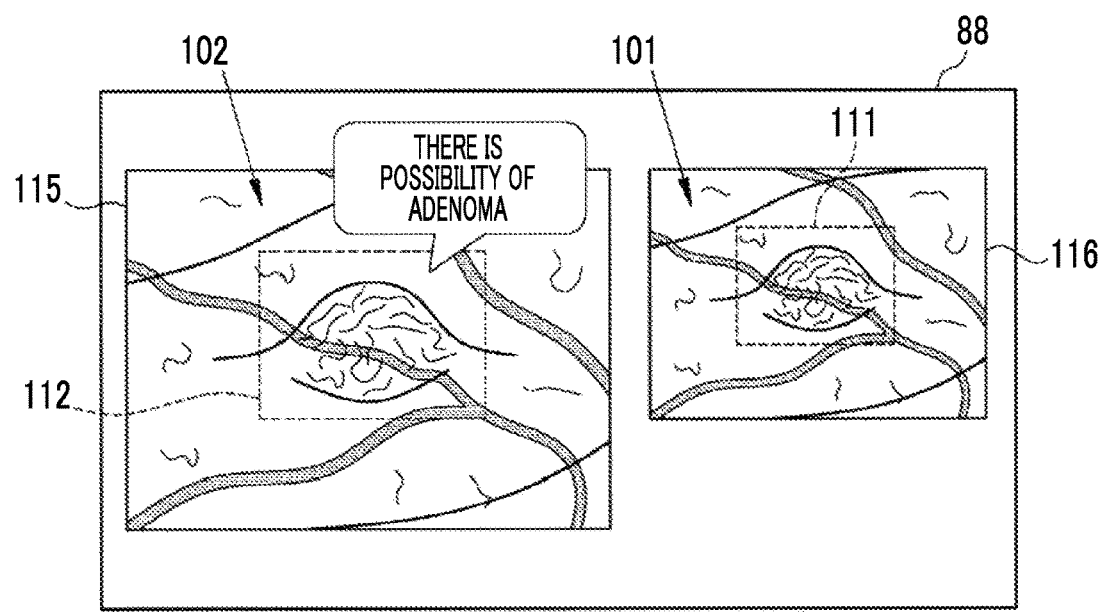
FIG. 17 is an explanatory diagram of a display form for displaying a determination result in a pop-up manner.

In the first to fourth embodiments described above, the monitor 88 includes the determination result display portion 117, and the determination result of the determination unit 85, such as "adenoma", is displayed in the determination result display portion 117 (refer to FIG. 5). However, the determination result of the determination unit 85 may be displayed using another method. For example, as shown in FIG. 17, the monitor 88 may display the determination result of the determination unit 85 in a pop-up manner, instead of the determination result display portion 117. In FIG. 17, a message showing the determination result is displayed in a pop-up manner. Instead, a value of the temporal change of the blood vessel index value Di, the blood vessel index value Di, and the like may be displayed in a pop-up manner as a determination result or together with the determination result.

The display setting of the above pop-up display may be performed using the temporal change of the blood vessel index value. For example, the display setting of display colors, such as the color of the contour of the pop-up display, the color of characters, and the color of the background, the font or thickness of characters, the line type or thickness of the contour line, and the like may be changed using the temporal change of the blood vessel index value Di, and the display content may be made to be noticeable according to an increase in the magnitude of the temporal change of the blood vessel index value Di.

Figure 18:
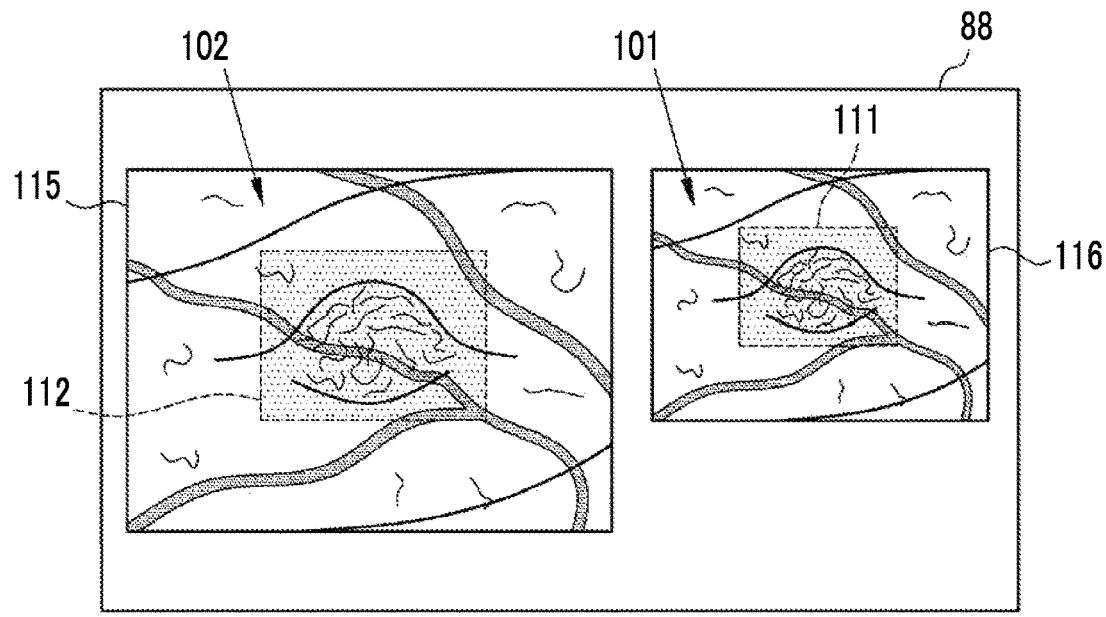
FIG. 18 is an explanatory diagram of a display form for displaying a determination result by coloring a portion where the state of the mucous membrane has been determined.

The monitor 88 may display the determination result of the determination unit 85 by displaying the first endoscope image 101 or the second endoscope image 102 in which a portion where the state of the mucous membrane has been determined using the determination result of the determination unit 85 is colored. For example, as shown in FIG. 18, the region of interest 111 or 112 where the state of the mucous membrane has been determined is colored. The color in a case where the state of the mucous membrane has been determined may be changed according to the determination result of the determination unit 85. For example, no color is applied in a case where the determination result is "normal", orange color is applied in a case where the determination result is "adenoma", and red color is applied in a case where the determination result is "cancer". In this manner, it is possible to display the determination result with good visibility together with the first endoscope image 101 or the second endoscope image 102.

Figure 19:
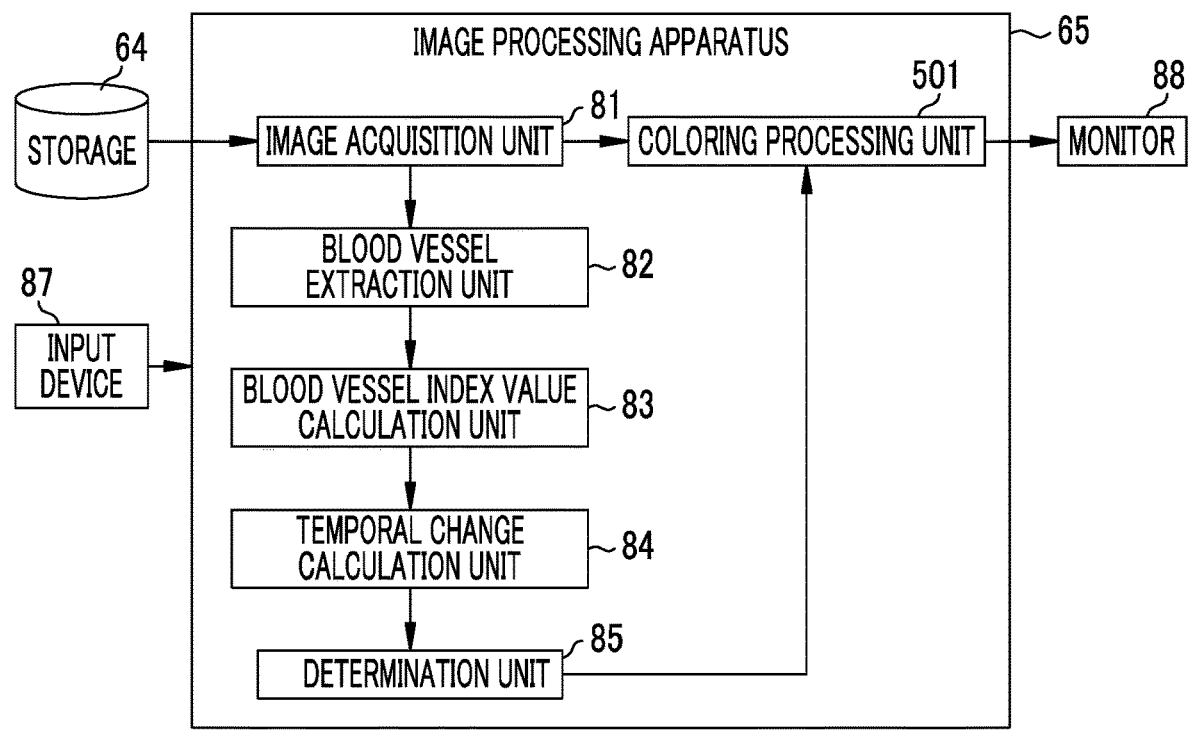
FIG. 19 is a block diagram of the image processing apparatus in the case of coloring a portion where the state of the mucous membrane has been determined.

In the case of displaying the first endoscope image 101 or the second endoscope image 102 in which a portion where the state of the mucous membrane has been determined is colored, the coloring processing unit 501 is provided in the image processing apparatus 65 as shown in FIG. 19. The coloring processing unit 501 performs the above-described coloring processing on the first endoscope image 101 or the second endoscope image 102 using information (position or range of the region of interest 111 and the region of interest 112) regarding the portion where the state of the mucous membrane has been determined and the determination result of the determination unit 85.

It is preferable that the color of the portion where the state of the mucous membrane has been determined is set using the temporal change calculated by the temporal change calculation unit 84 (in the first embodiment, the temporal change of the second blood vessel index value Di2 with respect to the first blood vessel index value Di1). In this case, the coloring processing unit 501 acquires the information of the temporal change calculated by the temporal change calculation unit 84 from the temporal change calculation unit 84. Then, the value of the temporal change calculated by the temporal change calculation unit 84 is compared with a threshold value (hereinafter, referred to as a third threshold value TH3), and a difference δ between the value of the temporal change calculated by the temporal change calculation unit 84 and the third threshold value TH3 is calculated.

Figure 20:
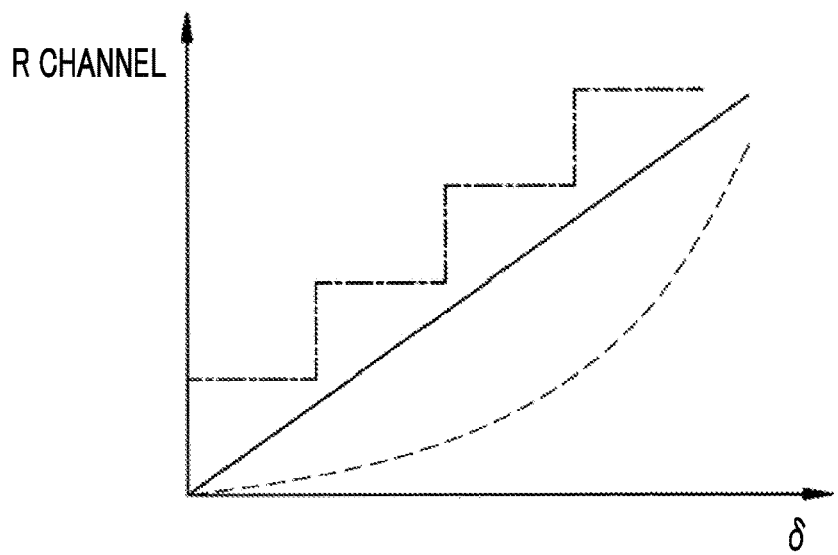
FIG. 20 is a graph showing the correspondence relationship between a difference δ from a threshold value and the value of an R channel.

Thereafter, for the color of the portion where the state of the mucous membrane has been determined in the first endoscope image 101 or the second endoscope image 102 displayed on the monitor 88, for example, as shown by the solid line in FIG. 20, the value of the R channel (red pixel of the image displayed on the monitor 88) is set in proportion to the difference δ. Although only the relationship between the difference δ and the R channel is shown in FIG. 20, the same is true for the B channel (blue pixel of the image displayed on the monitor 88) or the G channel (green pixel of the image displayed on the monitor 88). However, the relationship between the difference δ and the value of each channel may be changed for each RGB channel. The relationship between the difference δ and each channel may be set as a curve as shown by the broken line in FIG. 20, or may be set stepwise as shown by the one-dot chain line in FIG. 20. The relationship between the difference δ and each channel may be set by other functions or the like.

In the case of coloring a portion where the state of the mucous membrane has been determined as described above, In FIG. 18, the inside of each of the regions of interest 111 and 112 is colored so as to be shaded. However, only the frames of the regions of interest 111 and 112 may be colored, or not the entire regions of interest 111 and 112 but an abnormal portion (a portion with a determination result other than "normal") inside the regions of interest 111 and 112 may be selectively colored. An abnormal portion can be selected according to the blood vessel index value Di of each pixel, for example.

In the case of coloring a portion where the state of the mucous membrane has been determined as described above, the color of the portion where the state of the mucous membrane has been determined may be changed according to the blood vessel index value Di that is a basis for determining the abnormality. For example, coloring is performed with red type color in a case where the temporal change of the blood vessel density is an abnormal value, and coloring is performed with green type color in a case where the temporal change of the blood vessel thickness is an abnormal value. In this case, a priority is set in advance for each blood vessel index value Di, and a color set for the blood vessel index value Di with the higher priority is adopted in a case where two or more blood vessel index values Di are abnormal values.

Figure 21:
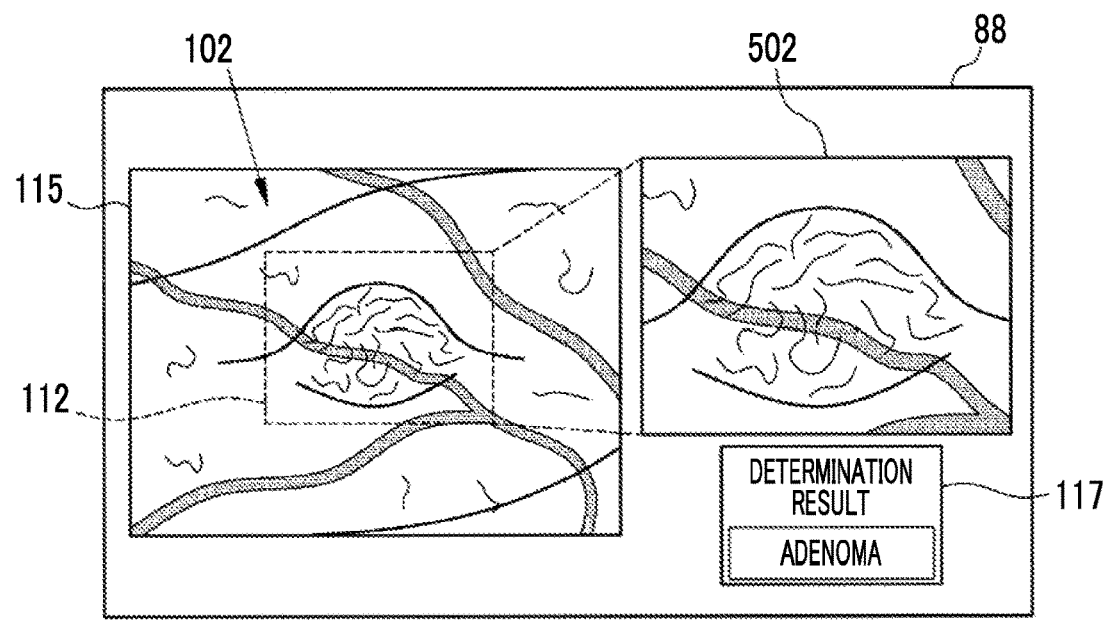
FIG. 21 is an explanatory diagram of a display form for displaying a portion, in which the state of the mucous membrane has been determined, in an enlarged manner.

In the first to fourth embodiments described above, the monitor 88 displays the determination result of the determination unit 85 in the determination result display portion 117 (refer to FIG. 5). However, as shown in FIG. 21, an enlarged image 502 obtained by enlarging a portion where the state of the mucous membrane has been determined may be displayed. In particular, in a case where the enlarged image 502 is displayed in a case where the determination result of the determination unit 85 is not "normal" (in the case of a determination result indicating any abnormality), the portion where the state of the mucous membrane has been determined can be easily examined in detail based on the determination result. Although the enlarged image 502 obtained by enlarging the portion where the state of the mucous membrane has been determined in the second endoscope image 102 is displayed on the monitor 88 in FIG. 21, an enlarged image obtained by enlarging a portion where the state of the mucous membrane has been determined in the first endoscope image 101 may be displayed.

It is preferable to set the enlargement ratio (the size of the enlarged image 502) of the portion where the state of the mucous membrane has been determined by using the temporal change of the blood vessel index value Di. For example, the enlargement ratio of the portion where the state of the mucous membrane has been determined may be made to increase as the temporal change of the blood vessel index value Di increases, so that the portion where the state of the mucous membrane has been determined is more noticeable.

The enlarged image 502 does not need to completely match the region of interest 112 where the state of the mucous membrane has been determined. For example, an enlarged image including a normal portion around the region of interest 112 where the state of the mucous membrane has been determined may be displayed. In FIG. 21, the enlarged image 502 is displayed instead of the subwindow 116 displaying the first endoscope image 101. However, the enlarged image 502 may be displayed in a pop-up manner, and the first endoscope image 101, the second endoscope image 102, and the determination result display portion 117 may be displayed in another display region.

In the first to fourth embodiments described above, the determination unit 85 determines the state of the mucous membrane of the observation target as one state. However, the determination unit 85 can determine the state of the mucous membrane of the observation target from a plurality of viewpoints. Specifically, since the blood vessel index value calculation unit 83 calculates a plurality of types of blood vessel index values Di (a plurality of kinds of blood vessel information Vi) and the temporal change calculation unit 84 calculates the temporal change of each of the plurality of types of blood vessel index values Di, the determination unit 85 can determine the state of the mucous membrane of the observation target from a plurality of viewpoints according to a method of combining the temporal changes of the plurality of types of blood vessel index values Di.

For example, the blood vessel index value calculation unit 83 calculates three types of blood vessel index values Di of a blood vessel index value DiA, a blood vessel index value DiB, and a blood vessel index value DiC, and the temporal change calculation unit 84 calculates a temporal change ΔA of the blood vessel index value DiA, a temporal change ΔB of the blood vessel index value DiB, and a temporal change ΔC of the blood vessel index value DiC. Then, it can be determined whether or not the state of the mucous membrane of the observation target is a lesion L1 by using the temporal changes ΔA and ΔB, and it can be determined whether the state of the mucous membrane of the observation target is a lesion L2 (for example, another lesion having a low relevance to the lesion L1) by using the temporal changes ΔA and ΔC. In such a case, the determination unit 85 can determine the state of the mucous membrane of the observation target from the first viewpoint of determining whether or not the state of the mucous membrane of the observation target is the lesion L1, and can determine the state of the mucous membrane of the observation target from the second viewpoint of determining whether or not the state of the mucous membrane of the observation target is the lesion L2.

Figure 22:
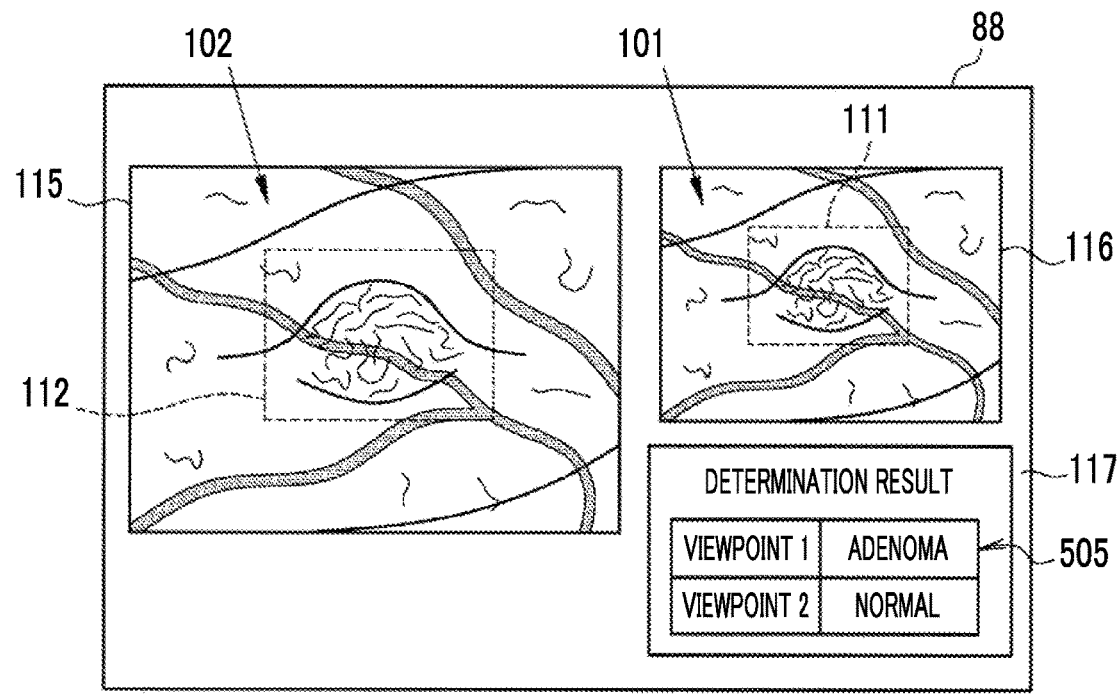
FIG. 22 is an explanatory diagram of a display form for displaying a list of determination results.

As described above, in a case where the determination unit 85 determines the state of the mucous membrane of the observation target from a plurality of viewpoints, it is preferable to display a determination result list 505, which shows the determination result at each viewpoint, in the determination result display portion 117 of the monitor 88 as shown in FIG. 22. In FIG. 22, a determination result ("adenoma") at the first viewpoint ("viewpoint 1") of using the temporal changes ΔA and ΔB and a determination result ("normal") at the second viewpoint ("viewpoint 2") of using the temporal changes ΔA and ΔC are displayed in the determination result list 505.

In the determination result list 505, all determination results including a determination result indicating "normal" are displayed. However, only a determination result indicating an abnormality (determination result other than "normal") may be displayed in the list 505.

The display setting of the determination result list 505 may be performed using the temporal change of the blood vessel index value Di. That is, display colors, such as the color of the contour of the list 505, the color of characters, and the color of the background, the font or thickness of characters, the line type or thickness of the contour line, and the like may be changed using the temporal change of the blood vessel index value Di, and the display content may be made to be noticeable according to an increase in the magnitude of the temporal change.

Although only the determination result at each viewpoint is displayed in the list 505, it is preferable to also display information other than the determination result in the list 505. For example, the coordinates of the mucous membrane as a determination target in the endoscope image, the blood vessel index value Di used in the determination, the value of the temporal change of the blood vessel index value Di, and the like may be displayed together with the determination result. In the case of determining the state of the mucous membrane using three or more endoscope images as in the fourth embodiment, in the case of a determination result indicating an abnormality (determination result other than "normal"), it is preferable to display the imaging time (start frame) of the endoscope image at which the determination result becomes abnormal first or the imaging time (end frame) of the endoscope image at which the determination result shows an abnormality last. Similarly, in the case of determining the state of the mucous membrane of the observation target in the length of the period Et during which the blood vessel index value Di satisfies specific conditions as in the modification example of the fourth embodiment, it is preferable to display a time (start time of the period Et) at which the blood vessel index value Di satisfies specific conditions first and a time (end time of the period Et) at which the blood vessel index value Di satisfies the specific conditions last. Various kinds of information that are preferably displayed in the list 505 together with the determination result may be displayed in a pop-up manner in a case where the determination result of the list 505 shown in FIG. 22 is selected, instead of displaying the various kinds of information in the list 505 together with the determination result from the beginning.

Figure 23:
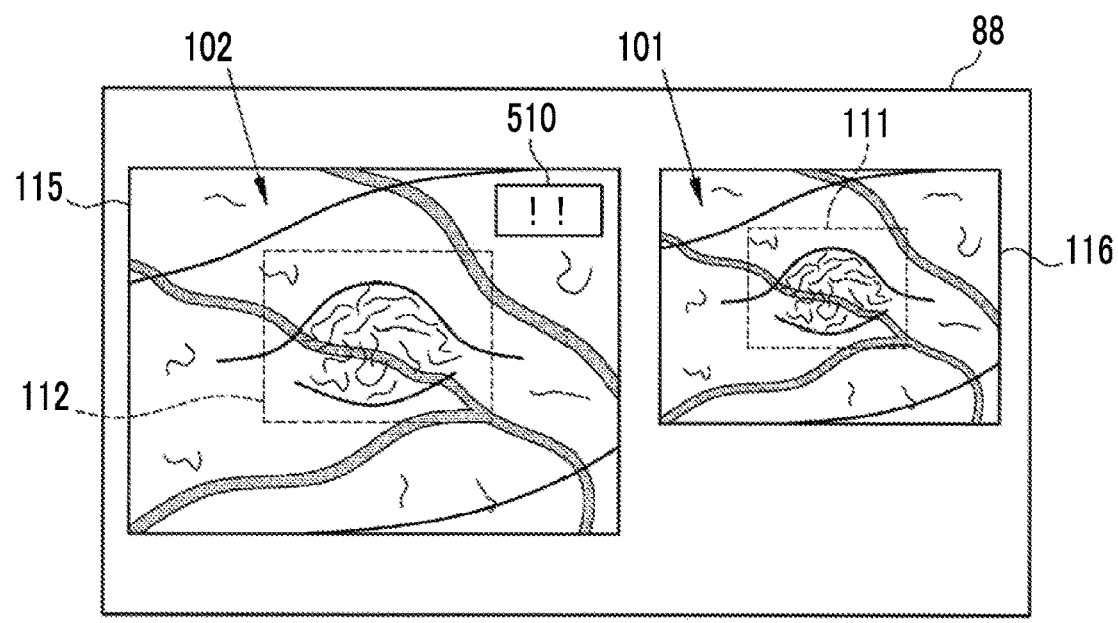
FIG. 23 is an explanatory diagram showing an operation menu for displaying a determination result.

Instead of the display of the determination results of the above-described various modification examples or the enlarged display of the portion where the state of the mucous membrane has been determined, an operation menu 510 (in FIG. 23, an icon "!!") may be displayed on the monitor 88 as shown in FIG. 23. Then, it is preferable that a doctor can select a required display from the display of the determination results of the above-described various modification examples, the enlarged display of the portion where the state of the mucous membrane has been determined, and the like by operating the operation menu 510. Although the operation menu 510 is displayed in the second endoscope image 102 in FIG. 23, the display position of the operation menu 510 is arbitrary. In addition, the display content or the display color of the text (in FIG. 23, "!!") of the operation menu 510 is arbitrary. The determination result of the determination unit 85 can be displayed in the operation menu 510. Similarly to the case of coloring a portion where the state of the mucous membrane has been determined (refer to FIG. 18), the display color of the operation menu 510 (color of the text displayed in the operation menu 510 or the color of the entire icon) may be changed according to the determination result of the determination unit 85.

It is desirable that the determination unit 85 determines the state of the mucous membrane to three or more states including normal, adenoma, and cancer. In particular, in the case of determining the state of the mucous membrane of the large intestine, it is preferable to determine the state of the mucous membrane of the large intestine to any state including normal, hyperplastic polyp (HP), sessile serrated adenoma/Polyp (SSA/P), traditional serrated adenoma (TSA), laterally spreading tumor (LST), and cancer. In a case where the determination result of the determination unit 85 is subdivided as described above, it is preferable that the determination unit 85 uses the value of the blood vessel index value Di in addition to the temporal change of the blood vessel index value Di. Conventionally, a hyperplastic polyp was thought to have low risk of canceration and does not need to be treated. In recent years, however, an example in which an SSA/P analogous to a hyperplastic polyp is cancerated has also been discovered. In particular, it is becoming important to differentiate between the hyperplastic polyp and the SSA/P. On the other hand, it is known that an SSA/P is likely to be formed in a case where the middle deep layer blood vessel 124 traverses under the thickened mucous membrane thought to be a hyperplastic polyp or SSA/P. By using the temporal change of the blood vessel index value Di, the determination unit 85 can differentiate between the hyperplastic polyp and the SSA/P. However, by performing determination using the temporal change of the blood vessel index value Di and the value of the blood vessel index value Di in combination, it is possible to differentiate between the hyperplastic polyp and the SSA/P with a higher probability.

In a case where the state of the mucous membrane of the observation target is cancer, it is preferable that the determination unit 85 further determines the stage of cancer using the temporal change of the blood vessel index value Di or using the temporal change of the blood vessel index value Di and the blood vessel index value Di in combination. Then, it is preferable to display the stage of the cancer determined by the determination unit 85 in the determination result display portion 117. In this manner, in a case where the state of the mucous membrane of the observation target is determined to be cancer, the stage is further determined and the result is displayed on the monitor 88, so that the diagnosis can be more finely assisted.

In the first to fourth embodiments described above, one region of interest is set for each endoscope image such as the first endoscope image 101 displayed on the monitor 88. However, a plurality of regions of interest may be set for each endoscope image such as the first endoscope image 101 displayed on the monitor 88. For example, each region obtained by dividing the entire endoscope image into meshes can be set as a region of interest, and the blood vessel index value Di and its temporal change can be calculated in each region of interest. In addition, the doctor may set an arbitrary number of regions of interest at arbitrary places.

Figure 24:
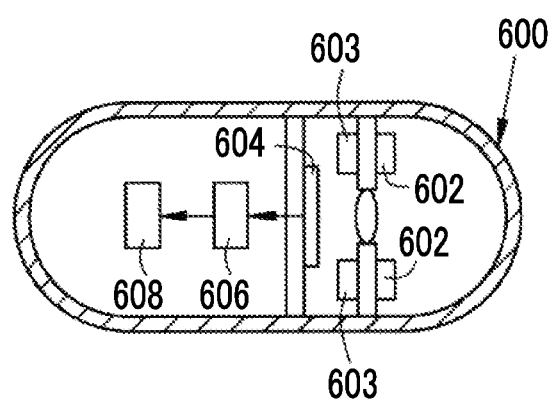
FIG. 24 is a schematic diagram of a capsule endoscope.

In the first to fourth embodiments and the various modification examples described above, the present invention is implemented by the endoscope system 10 (or the endoscope system 310) that performs observation by inserting the endoscope 12, in which the imaging sensor 48 is provided, into the subject. However, the present invention is also suitable for a capsule endoscope system. For example, as shown in FIG. 24, a capsule endoscope system includes at least a capsule endoscope 600 and a processor device (not shown). The capsule endoscope 600 includes a light source 602, a light source control unit 603, an imaging sensor 604, an image signal acquisition processing unit 606, and a transmitting and receiving antenna 608. The light source 602 is configured similarly to the light source 20 of the endoscope system 10, and emits illumination light under the control of the light source control unit 603. The image signal acquisition processing unit 606 functions as the image signal acquisition unit 53, the DSP 56, the noise reduction unit 58, and the signal processing unit 62. The processor device of the capsule endoscope system is configured similarly to the processor device 16 of the endoscope system 310, and also functions as the image processing apparatus 65.

EXPLANATION OF REFERENCES

10: endoscope system
12: endoscope
12a: insertion part
12b: operation unit
12c: bending portion
12d: distal end portion
12e: angle knob
13a: still image acquisition instruction unit
13b: zoom operation unit
14: light source device
16: processor device
18: monitor
19: console
20: light source
22: light source control unit
30a: illumination optical system
30b: imaging optical system
41: light guide
45: illumination lens
46: objective lens
47: zoom lens
48: imaging sensor
51: CDS/AGC circuit
52: A/D converter
53: image signal acquisition unit
56: DSP
58: noise reduction unit
61: memory
62: signal processing unit
63: video signal generation unit
64: storage
65: image processing apparatus
81: image acquisition unit
82: blood vessel extraction unit
83: blood vessel index value calculation unit
84: temporal change calculation unit
85: determination unit
87: input device
88: monitor
99: endoscope image
101: first endoscope image
102: second endoscope image
103: third endoscope image
111: first region of interest
112: second region of interest
115: main window
116: subwindow
117: determination result display portion
122: shape of mucosal surface
123: surface layer blood vessel
124: middle deep layer blood vessel
132: second blood vessel image
251: blood vessel information calculation unit
252: blood vessel parameter calculation unit
253: weighting coefficient table
310: endoscope system
403: third endoscope image
411: first region of interest
412: second region of interest
413: third region of interest
414: main window
415: first subwindow
416: second subwindow
501: coloring processing unit
502: enlarged image
505: determination result list
510: operation menu
600: capsule endoscope
602: light source
603: light source control unit
604: imaging sensor
606: image signal acquisition processing unit
608: transmitting and receiving antenna
di: blood vessel index value
Di: blood vessel index value
Di: first blood vessel index value
Di: second blood vessel index value
di1: first blood vessel index value
Di1: first blood vessel index value
di2: second blood vessel index value
Di2: second blood vessel index value
Di3: third blood vessel index value
DiA: blood vessel index value
DiB: blood vessel index value
DiC: blood vessel index value
Et: period
L1: lesion
L2: lesion
P: index value
P1: blood vessel parameter
P2: blood vessel parameter
Ri: region
Ro: region
T1: imaging time T2: imaging time
T3: imaging time
TH1: first threshold value
TH2: second threshold value
TH3: third threshold value
Vi: blood vessel information

What is claimed is:

1. An image processing apparatus, comprising:
a storage for storing a plurality of endoscope images;
a processor device, connected with the storage, wherein the processor device is configured to:
acquire the plurality of endoscope images obtained by imaging an observation target at different times with an endoscope;
extract blood vessels of the observation target from the plurality of endoscope images;
calculate a plurality of types of a blood vessel index value for each of the blood vessels extracted from the endoscope images;
calculate a temporal change of the blood vessel index value for each type of the blood vessel index value; and
determine a state of a mucous membrane of the observation target using the temporal change for each type of the blood vessel index value; and
a display unit that displays a determination result of the determination unit.

2. The image processing apparatus according to claim 1, wherein the processor device calculates, as the blood vessel index value, any blood vessel information of the number of blood vessels extracted by the processor device, a thickness, a change in thickness, complexity of thickness change, a length, a change in length, the number of branches, a branching angle, a distance between branch points, the number of crossings, an inclination, an area, a density, a depth with respect to a mucous membrane as a reference, a height difference, an interval, a contrast, a color, a color change, a degree of meandering, blood concentration, oxygen saturation, a proportion of arteries, a proportion of veins, concentration of administered coloring agent, a running pattern, and a blood flow rate.

3. The image processing apparatus according to claim 1, wherein the processor device is further configured to:
calculate any blood vessel information of the number of blood vessels extracted by the processor device, a thickness, a change in thickness, complexity of thickness change, a length, a change in length, the number of branches, a branching angle, a distance between branch points, the number of crossings, an inclination, an area, a density, a depth with respect to a mucous membrane as a reference, a height difference, an interval, a contrast, a color, a color change, a degree of meandering, blood concentration, oxygen saturation, a proportion of arteries, a proportion of veins, concentration of administered coloring agent, a running pattern, and a blood flow rate; and
calculate a blood vessel parameter by calculation using a plurality of pieces of the blood vessel information, and the processor device sets the blood vessel parameter as the blood vessel index value.

4. The image processing apparatus according to claim 1, wherein the processor device calculates a difference, a ratio, or a change rate between a plurality of the blood vessel index values.

5. The image processing apparatus according to claim 1, wherein the processor device determines the state of the mucous membrane of the observation target based on a combination of temporal changes of the blood vessel index values in a plurality of time sections.

6. The image processing apparatus according to claim 1, wherein the processor device calculates a length of a period during which the blood vessel index value is equal to or greater than a threshold value or the blood vessel index value is less than the threshold value, and determines the state of the mucous membrane of the observation target based on the calculated length of the period.

7. The image processing apparatus according to claim 1, wherein, in a case of setting a region of interest in the plurality of endoscope images,
the processor device not only calculates the blood vessel index value of the region of interest but also calculates the blood vessel index value of a region outside the region of interest,
the processor device calculates a spatial change of the blood vessel index value using the blood vessel index values of the inside and outside of the region of interest, and calculates a temporal change of the spatial change of the blood vessel index value, and
the processor device determines the state of the mucous membrane based on the temporal change of the spatial change of the blood vessel index value.

8. The image processing apparatus according to claim 1, wherein the determination result of the processor device is displayed in a pop-up manner on the display unit.

9. The image processing apparatus according to claim 8, wherein display setting of the pop-up display is performed using the temporal change of the blood vessel index value.

10. The image processing apparatus according to claim 1, wherein the endoscope image in which a portion where the state of the mucous membrane has been determined using the determination result of the processor device is colored is displayed on the display unit.

11. The image processing apparatus according to claim 10, wherein, on the display unit, a color of a portion to be colored in the endoscope image is set using the temporal change of the blood vessel index value.

12. The image processing apparatus according to claim 1, wherein a list of the determination result of the processor device is displayed on the display unit.

13. The image processing apparatus according to claim 12, wherein display setting of the list is performed using the temporal change of the blood vessel index value.

14. The image processing apparatus according to claim 1, wherein a portion where the state of the mucous membrane of the endoscope image has been determined is displayed in an enlarged manner on the display unit.

15. The image processing apparatus according to claim 14, wherein an enlargement ratio of the portion where the state of the mucous membrane of the endoscope image has been determined is set using the temporal change of the blood vessel index value.

16. An endoscope system, comprising:
an endoscope that images an observation target;
a processor device being configured to acquire a plurality of endoscope images obtained by imaging the observation target at different times with the endoscope, to extract blood vessels of the observation target from the plurality of endoscope images, to calculate a plurality of types of a blood vessel index value for each of the blood vessels extracted from the endoscope images, to calculate a temporal change of the blood vessel index value for each type of the blood vessel index value, and to determine a state of a mucous membrane of the observation target using the temporal change for each type of the blood vessel index value; and a display unit that displays a determination result of the determination unit.

17. An image processing method, comprising:

acquiring a plurality of endoscope images obtained by imaging an observation target at different times with an endoscope by an image processing apparatus;

extracting blood vessels of the observation target from the plurality of endoscope images by the image processing apparatus;

calculating a plurality of types of a blood vessel index value for each of the blood vessels extracted from the endoscope images by the image processing apparatus;

calculating a temporal change of the blood vessel index value for each type of the blood vessel index value by the image processing apparatus; and determining a state of a mucous membrane of the observation target using the temporal change for each type of the blood vessel index value by the image processing apparatus.

* * * * *